(12) United States Patent
Rajaraman et al.

(10) Patent No.: US 12,085,557 B2
(45) Date of Patent: Sep. 10, 2024

(54) FABRICATION OF 3D MICROELECTRODES AND USE THEREOF IN MULTI-FUNCTIONAL BIOSYSTEMS

(71) Applicant: UNIVERSITY OF CENTRAL FLORIDA RESEARCH FOUNDATION, INC., Orlando, FL (US)

(72) Inventors: Swaminathan Rajaraman, Winter Park, FL (US); Lei Zhai, Oviedo, FL (US); Avra Kundu, Orlando, FL (US); Nilab Azim, Ovideo, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 1232 days.

(21) Appl. No.: 16/404,729

(22) Filed: May 6, 2019

(65) Prior Publication Data

US 2019/0360995 A1 Nov. 28, 2019

Related U.S. Application Data

(60) Provisional application No. 62/667,589, filed on May 6, 2018.

(51) Int. Cl.
*G01N 33/48* (2006.01)
*B01L 3/00* (2006.01)
(Continued)

(52) U.S. Cl.
CPC ........ *G01N 33/4836* (2013.01); *B01L 3/5085* (2013.01); *B29C 64/124* (2017.08);
(Continued)

(58) Field of Classification Search
CPC ......... G01N 33/4836; B01L 2300/0645; B01L 2300/0636; B81C 1/00111; B81B 1/008;
(Continued)

(56) References Cited

U.S. PATENT DOCUMENTS

2008/0138581 A1* 6/2008 Bhandari .................. G03F 7/16
428/156
2008/0150556 A1* 6/2008 Han ....................... B82Y 15/00
977/762
(Continued)

FOREIGN PATENT DOCUMENTS

KR       20180021401 A  *  3/2018
WO    WO-2017203685 A1  *  11/2017  ........... A61B 5/0408
WO    WO-2018184104 A1  *  10/2018  ............... A61B 5/04

OTHER PUBLICATIONS

Machine translation of KR 20180021401 A, obtained from KIPO.*
(Continued)

*Primary Examiner* — Z. Jim Yang
(74) *Attorney, Agent, or Firm* — Timothy H. Van Dyke; WOLTER, VAN DYKE, DAVIS, PLLC

(57) ABSTRACT

Disclosed herein is a microelectrode platform that may be used for multiple biosystem applications including cell culturing techniques and biosensing. Also disclosed are microfabrication techniques for inexpensively producing microelectrode platforms.

13 Claims, 10 Drawing Sheets

(51) Int. Cl.

| | |
|---|---|
| *B29C 64/124* | (2017.01) |
| *B33Y 10/00* | (2015.01) |
| *C12M 1/34* | (2006.01) |
| *C12M 3/00* | (2006.01) |
| *C12N 1/38* | (2006.01) |
| *C12N 13/00* | (2006.01) |
| *D01D 5/00* | (2006.01) |
| *G01N 27/12* | (2006.01) |
| *G01N 27/27* | (2006.01) |
| *G01N 33/483* | (2006.01) |
| *C08K 3/08* | (2006.01) |
| *H01L 23/29* | (2006.01) |

(52) U.S. Cl.
CPC ........... *B33Y 10/00* (2014.12); *C12M 1/3407* (2013.01); *C12M 3/00* (2013.01); *C12M 41/46* (2013.01); *C12N 1/38* (2013.01); *C12N 13/00* (2013.01); *D01D 5/0007* (2013.01); *G01N 27/128* (2013.01); *G01N 27/27* (2013.01); *B01L 2300/0645* (2013.01); *C08K 2003/0806* (2013.01); *H01L 23/293* (2013.01); *Y10T 428/24339* (2015.01)

(58) Field of Classification Search
CPC ............ B81B 2201/055; B81B 2203/04; B01J 2219/00659; B01J 2219/00662; A61B 5/25; A61B 5/262; A61B 5/263; A61B 5/685

See application file for complete search history.

(56) References Cited

U.S. PATENT DOCUMENTS

| | | | |
|---|---|---|---|
| 2016/0047770 A1 | 2/2016 | Tyler et al. | |
| 2016/0320365 A1* | 11/2016 | Tsuji | G01N 33/4836 |
| 2019/0380603 A1* | 12/2019 | Schouenborg | A61N 1/0551 |
| 2020/0164107 A1* | 5/2020 | Xie | A61L 27/60 |
| 2020/0323453 A1* | 10/2020 | Lee | H05K 1/118 |
| 2020/0393438 A1* | 12/2020 | Wijdenes | A61B 5/291 |
| 2022/0096706 A1* | 3/2022 | Xie | A61L 15/26 |

OTHER PUBLICATIONS

Xiao, et al., "Immobilization of Zerovalent Iron Nanoparticles into Electrospun Polymer Nanofibers: Synthesis, Characterization, and Potential Environmental Applications," J. Phys. Chem. C, Oct. 2009, pp. 18062-18068, vol. 113, No. 42.

Xie, et al., "Radially Aligned, Electrospun Nanofibers as Dural Substitutes for Wound Closure and Tissue Regeneration Applications," ACS Nano, Sep. 2010, pp. 5027-5036, vol. 4, No. 9.

Zorlutuna, et al., "Microfabricated Biomaterials for Engineering 3D Tissues," Adv. Mater., Apr. 2012, pp. 1782-1804, vol. 24, No. 14.

Abou El-Nour, et al., "Synthesis and applications of silver nanoparticles," Arab. J. Chem., Jul. 2010, pp. 135-140, vol. 3, No. 3.

Alf et al., "Chemical vapor deposition of conformal, functional, and responsive polymer films," Adv. Mater., Dec. 2010, pp. 1993-2027, vol. 22, No. 18.

An et al., "Developing robust, hydrogel-based, nanofiber-enabled encapsulation devices (NEEDs) for cell therapies," Biomaterials, Jan. 2015, pp. 40-48, vol. 37.

Atthi et al., "Improvement of Photoresist Film Coverage on High Topology Surface with Spray Coating Technique," 2010, pp. 42-46.

Azim, et al., "Fabrication and Characterization of a 3D Printed, MicroElectrodes Platform with Functionalized Electrospun Nano-Scaffolds and Spin Coated 3D Insulation Towards Multi-Functional Biosystems," J. of MicroElec Systems, 2019, pp. 1-13.

Azim, et al., "Fabrication and Characterization of 3D Printed, 3D Microelectrode Arrays With Spin Coated Insulation and Functional Electrospun 3D Scaffolds for 'Disease in a Dish' and 'Organ on a Chip' Models," Solid-State Sensors, Actuators and Microsystems Workshop, 2018, pp. 124-127.

Baji, et al., "Electrospinning of polymer nanofibers: Effects on oriented morphology, structures and tensile properties," Compos. Sci. Technol., 2010, pp. 703-718, vol. 70, No. 5.

Bauer, et al., "Antibiotic susceptibility testing by a standardized single disk method.," Am. J. Clin. Pathol., Apr. 1966., pp. 493-496, vol. 45, No. 4.

Bhardwaj et al., "Electrospinning: A fascinating fiber fabrication technique," Biotechnol. Adv., May 2010, pp. 325-347, vol. 28, No. 3.

Blau, "Cell adhesion promotion strategies for signal transduction enhancement in microelectrode array in vitro electrophysiology: An introductory overview and critical discussion," Curr. Opin. Colloid Interface Sci., Oct. 2013, pp. 481-492, vol. 18, No. 5.

Borkholder, "Cell Based Biosensors using Microelectrodes," PHD thesis, 1998, pp. 1-253.

Borkholder, et al., "Microelectrode arrays for stimulation of neural slice preparations," J. Neurosci. Methods, Nov. 1997, pp. 61-66, vol. 77, No. 1.

Cao, et al., "Threedimensional culture of human mesenchymal stem cells in a polyethylene terephthalate matrix," Biomed. Mater., Dec. 2010, pp. 1-8, vol. 5, No. 6.

Chunder, et al., "Fabrication of ultrathin polyelectrolyte fibers and their controlled release properties," Colloids Surfaces B Biointerfaces, Aug. 2007, pp. 172-179, vol. 58, No. 2.

Diaz, et al., "Tissue Engineering Scaffolds for 3D Cell Culture," Humana Press, 2016, pp. 249-268.

Duran, et al., "Silver nanoparticles: A new view on mechanistic aspects on antimicrobial activity," Nanomedicine Nanotechnology, Biol. Med., Apr. 2016, pp. 789-799, vol. 12, No. 3.

Duval et al., "Modeling Physiological Events in 2D vs. 3D Cell Culture," Physiology, Jul. 2017, pp. 266-277, vol. 32, No. 4.

Formlabs, "Materials Data Sheet Photopolymer Resin for Form 1+ and Form 2 Formlabs Material Properties," 2017, pp. 1-6.

Franks, et al. "Impedance characterization and modeling of electrodes for biomedical applications," IEEE Trans. Biomed. Eng., Jul. 2005, pp. 1295-1302, vol. 52, No. 7.

Frazier, et al., "High aspect ratio electroplated microstructures using a photosensitive polyimide process," in [1992] Proceedings IEEE Micro Electro Mechanical Systems, 1992, pp. 87-92.

Ghane-Motlagh, et al., "Design and Implementation Challenges of Microelectrode Arrays: A Review," Mater. Sci. Appl., Jul. 2013, pp. 483-495, vol. 04, No. 08.

Ginger, et al., "The Evolution of Dip-Pen Nanolithography," Angew. Chemie—Int. Ed., Jan. 2004, pp. 30-45, vol. 43, No. 1.

Hong, et al., "Preparation of antimicrobial poly(vinyl alcohol) nanofibers containing silver nanoparticles," J. Polym. Sci. Part B Polym. Phys., Sep. 2006, pp. 2468-2474, vol. 44, No. 17.

Justice, et al., "3D cell culture opens new dimensions in cell-based assays," Drug Discov. Today, Jan. 2009, pp. 102-107, vol. 14, No. 1-2.

Kim, et al. "Recent trends in microelectrode array technology for in vitro neural interface platform," Biomed. Eng. Lett., Jun. 2014 pp. 129-141, vol. 4, No. 2.

Knight, et al., "Advances in 3D cell culture technologies enabling tissue-like structures to be created in vitro," J. Anat., Dec. 2015, pp. 746-756, vol. 227, No. 6.

Kumagai, et al., "Photoresist spray coating for 3D MEMS/NEMS," in 2012 IEEE Nanotechnology Materials and Devices Conference, IEEE NMDC 2012, 2012, pp. 124-127.

Kundu, et al., "3D Printing, Ink Casting and Micromachined Lamination (3D PICLµM): A Makerspace Approach to the Fabrication of Biological Microdevices," Micromachines, Feb. 2018, pp. 1-23, vol. 9, No. 2.

Lannutti, et al., "Electrospinning for tissue engineering scaffolds," Mater. Sci. Eng. C, Apr. 2007, pp. 504-509, vol. 27, No. 3.

Li, et al., "Thermal compression and characterization of three-dimensional nonwoven PET matrices as tissue engineering scaffolds," Biomaterials, Mar. 2001, pp. 609-618, vol. 22, No. 6.

(56) References Cited

OTHER PUBLICATIONS

Liu et al., "Electrospun Three-Dimensional Nanofibrous Structure via Probe Arrays Inducing," Micromachines, Aug. 2018, pp. 1-9, vol. 9, No. 9.

Ma, et al., "Surface engineering of electrospun polyethylene terephthalate (PET) nanofibers towards development of a new material for blood vessel engineering," Biomaterials, May 2005, pp. 2527-2536, vol. 26, No. 15.

Malhotra, et al., "Bioinspired Metal Ion Coordinated Polyelectrolyte Fibrous Nanoreactors," Adv. Mater. Interfaces, Nov. 2016 pp. 1-10, vol. 3, No. 22.

Masi et al., "Electrical spiking in bacterial biofilms," J. R. Soc. Interface, 2014,pp. 1-10, vol. 12, No. 102.

Nargang et al., "Liquid polystyrene: a room-temperature photocurable soft lithography compatible pour-and-cure-type polystyrene," Lab Chip, Jul. 2014, pp. 2698-2708, vol. 14, No. 15.

Park et al., "Electrospun poly(vinyl alcohol) nanofibers: effects of degree of hydrolysis and enhanced water stability," Polym. J., Mar. 2010, pp. 273-276, vol. 42, No. 3.

Pham, J. N. Burghartz, and P. M. Sarro, "Spray coating of photoresist for pattern transfer on high topography surfaces," J. Micromechanics Microengineering, Apr. 2005, pp. 691-697, vol. 15, No. 4.

Qian, et al., "Fluorescence imaging of metal ions implicated in diseases," Chem. Soc. Rev., Jul. 2015, pp. 4487-4493, vol. 44, No. 14.

Rai, et al., "Silver nanoparticles as a new generation of antimicrobials," Biotechnol. Adv., Jan. 2009, pp. 76-83, vol. 27, No. 1.

Rajaraman et al., "Microfabrication technologies for a coupled three-dimensional microelectrode, microfluidic array," J. Micromechanics Microengineering, Jan. 2007, pp. 163-171, vol. 17,No. 1.

Rajaraman et al., "Three-Dimensional Metal Transfer Micromolded Microelectrode Arrays (MEAS) for In-Vitro Brain Slice Recordings," in Transducers 2007-2007 International Solid-State Sensors, Actuators and Microsystems Conference, 2007, pp. 1251-1254.

Rajaraman, et al., "Metal-Transfer-Micromolded Three-Dimensional Microelectrode Arrays for in-vitro Brain-Slice Recordings," J. Microelectromechanical Syst., Apr. 2011, pp. 396-409, vol. 20, No. 2.

Ruther et al., "The NeuroProbes Project-Multifunctional Probe Arrays for Neural Recording and Stimulation," Proc. 13th Annu. Conf. IFESS, Sep. 21-25, Freiburg, Ger., 2008, pp. 238-240, vol. 53.

Santiago-Morales, et al., "Antimicrobial activity of poly(vinyl alcohol)-poly(acrylic acid) electrospun nanofibers," Colloids Surfaces B Biointerfaces, Oct. 2016, pp. 144-151, vol. 146.

Shmoel, et al., "Multisite electrophysiological recordings by self-assembled loose-patch-like junctions between cultured hippocampal neurons and mushroom-shaped microelectrodes," Sci. Rep., Jul. 2016, pp. 1-11, vol. 6, No. 1.

Sileo et al., "Electrical coupling of mammalian neurons to microelectrodes with 3D nanoprotrusions," Microelectron. Eng., Nov. 2013, pp. 384-390, vol. 111.

Son, et al., "Silver-polydopamine hybrid coatings of electrospun poly(vinyl alcohol) nanofibers," Macromol. Mater. Eng., May 2013, pp. 547-554, vol. 298, No. 5.

Tibbitt, et a., "Hydrogels as extracellular matrix mimics for 3D cell culture," Biotechnol. Bioeng., Jul. 2009, pp. 655-663, vol. 103, No. 4.

Wang et al., "Enhancing the hydrophilicity and cell attachment of 3D printed PCL/graphene scaffolds for bone tissue engineering," Materials (Basel)., Dec. 2016, pp. 1-11, vol. 9, No. 12.

Watt, et al., "Role of the extracellular matrix in regulating stem cell fate," Nat. Rev. Mol. Cell Biol., Aug. 2013, pp. 467-473, vol. 14, No. 8.

\* cited by examiner

Culture well

Bio-compatible Laminate

Stencil mask 3D printed 3D MEA: Ti/Au electrodes and traces

Close-up view of the ten recording sites of a single patch

FABRICATION OF 3D MICROELECTRODES AND USE THEREOF IN MULTI-FUNCTIONAL BIOSYSTEMS

GOVERNMENT SUPPORT

This invention was made with Government support under agency contract/grant nos. 1462895 and 1560007 awarded by the National Science Foundations. The Government has certain rights in this invention.

BACKGROUND

Exploring the dynamics that coordinate cellular microenvironments where complex signaling pathways result in tissue formation, function and pathophysiology has found great interest in recent years. As the tissue environment is essentially three dimensional (3D), there is an increasing need to extend cell culture matrices, support scaffolds and microelectrodes to 3D as well [1]. 3D cell cultures enable the formation of dynamic, spatial gradients of soluble factors that influence cellular migration, cell to cell communication and differentiation [2]. 3D cell cultures can be achieved through scaffold and scaffold-free approaches. Scaffold-free approaches include aggregate cultures or spheroids, whereas scaffold approaches typically consist of hydrogels or solid polymeric support materials [3]-[6]. Scaffolds are meant to surrogate the missing tissue specialized extracellular matrix (ECM), which plays a key role in cell attachment, tissue homeostasis, growth, proliferation, differentiation, morphology, polarization, directional motility, migration and cell spreading [3]-[8]. While some cells are able to synthesize all required ECM components, others require an external source, particularly when grown in serum-free culture media. Therefore, the synthetic ECM must mimic the extracellular environment of the host as best as possible [9]. This would reduce the large mismatch between chemical, biomechanical and textural properties of cells and synthetic interfacing devices such as Microelectrode Arrays (MEAs). As a result, a more stable and functionally predictable interfacial interaction between the cell and its environment, especially ECM, has a profound effect on cell phenotype and fate. Therefore, the chemical, topographical and elastomechanical properties of non-biological substrate surfaces that are supposed to be in intimate contact with cells or tissue needs careful engineering.

BRIEF DESCRIPTION OF THE DRAWINGS

These and other features, aspects, and advantages of the present disclosure will become better understood with reference to the following description and appended claims, and accompanying drawings where:

GENERAL TERMS

Figure 1:
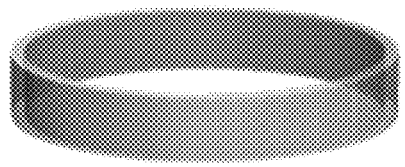
FIG. 1: Exploded view of schematics for the microfabrication of a 3D MEA: 3D printed microtowers, stencil mask metallization, laminate insulation and 3D printed, containment culture well with a close-up of the ten recording sites per patch.
Figure 1:
Figure 1:
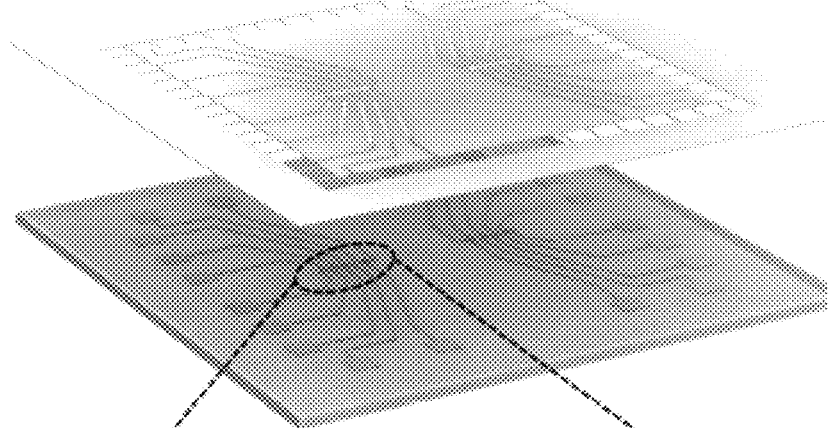
Figure 1:
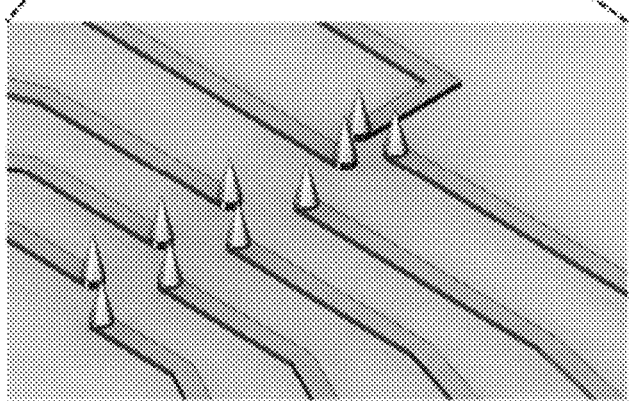

It is to be noted that the terms "first," "second," and the like as used herein do not denote any order, quantity, or importance, but rather are used to distinguish one element from another. The terms "a" and "an" do not denote a limitation of quantity, but rather denote the presence of at least one of the referenced item.

The terminology used herein is for the purpose of describing particular embodiments only and is not intended to be limiting. As used herein, the singular forms "a," "an," and "the" are intended to include the plural forms as well, unless the context clearly indicates otherwise these terms do not denote a limitation of quantity, but rather denote the presence of at least one of the referenced item. Furthermore, to the extent that the terms "including," "includes," "having," "has," "with," or variants thereof are used in either the detailed description and/or the claims, such terms are intended to be inclusive in a manner similar to the term "comprising."

The term "about" or "approximately" is meant to denote up to a 5, 6, 7, 8, 9, or 10 percent variance in the stated value or range. For example, about 2 includes values of 1.9 to 2.1.

The term "microscale" is meant to denote a size of from 1-1000 micrometers.

DETAILED DESCRIPTION

Embodiments disclosed herein include a novel microelectrode platform that has numerous important applications such as:
- Lab-on-a-chip applications
- Disease modeling applications
- Neuropharmacological testing
- Cardiotoxicity assessment
- Pre-clinical drug discovery
- High throughput phenotypic screening of drug candidates The microelectrode platforms described herein may not only be useful as a sensing (recording) and stimulation platform, but also a drug/therapeutic delivery system. The additional functionality of drug loaded nanofibers has made it possible for microelectrode platforms to simultaneously release molecules and act as a sensor, rendering the disclosed embodiments versatile and applicable in a large range of markets.

Also disclosed herein are novel fabrication methods for 3D microelectrode platforms that are fully functional for 3D cell culture applications. In one embodiment, the microfabrication method involves producing 3D metallized microtowers realized by 3D printing, metal evaporation and biocompatible laminate layer to insulate the traces. Electrospun 3D nanofiber scaffolds (NFS) are coupled to the microelectrodes to provide additional functionality. The scaffolds may be formed via electrospinning two types of nanofibers: ~200-500 nm PET, a hydrophobic polymer, and ~100 nm PVA/PAA, a hydrophilic co-polymer. PVA/PAA nanofibers had consistent diameters without beading and were used in subsequent experiments. Impedance measurements before, 651.3 kΩ, and after, 659.4 kΩ, deposition of PVA/PAA remains unchanged, indicating enhanced functionality without interfering with the electrical characteristics of the 3D MEAs.

In a specific embodiment, silver nanoparticles (AgNPs) were embedded as model drug compounds in the PVA/PAA NFS to demonstrate the potential of the 3D MEA as a biosensor and drug delivery system. TEM and antimicrobial studies demonstrated ~5-15 nm Ag NPs within the PVA/PAA NFS, which was potent to *Acinetobacter baumannii* and *Escherichia coli*. Use of the silver nanoparticles demonstrates that other bioactive agents can be embedded in the nano Fine 3D insulation atop the microtowers was achieved using a dropcasted/spin-coated 3D layer of Polystyrene (PS). The layer of PS may be ablated (such as via laser micromachining) to realize smaller electrodes, e.g., 50×50 µm² 3 D microelectrodes, with impedance properties similar to other reported approaches.

Accordingly, in one embodiment, disclosed is a microelectrode platform that includes a plurality of metallized microtower electrodes, wherein each of the plurality of metallized microtower electrodes comprises a tip, a metallic layer disposed on each of the plurality of metallized microtower electrodes; a biocompatible laminate layer disposed on the metallic layer, wherein the biocompatible laminate layer comprises a plurality of micromachined apertures arranged to correspond with the tip of each of the plurality of metallized microtower electrodes; and a plurality of interconnected nano-scaffolds disposed in a three-dimensional pattern above the tip of each of the plurality of metallized microtower electrodes. In a specific embodiment, the metallic layer includes titanium or gold, or combinations thereof. In another specific embodiment, the metallic layer has a thickness of from about 10 nm to about 100 nm.

The plurality of interconnected nano-scaffolds may comprise one selected from the group consisting of polyvinyl alcohol (PVA), polyacrylic acid (PAA), polyethylene terephthalate (PET), combinations thereof, and copolymers thereof. The nano-scaffolds may further include one or more bioactive agents embedded therein. Examples of bioactive agents include a drug, antimicrobial agent, an antiviral agent, an antibiotic agent, and combinations thereof. In a specific embodiment, the bioactive agent includes nanoparticles, such as silver nanoparticles. The microelectrode platform nano-scaffolds may exhibit an inhibitory effect toward bacteria, viruses or other microbials.

In a specific embodiment, the biocompatible laminate layer comprises an insulating polymeric material. One example of a suitable insulating polymeric material includes, but is not limited to, polysterene.

According to another embodiment, disclosed is a method for producing a microelectrode platform that involves 3D-printing a plurality of microtower electrodes, wherein each of the plurality of microtower electrodes comprises a tip; metallizing the plurality of microtower electrodes via physical vapor deposition of a metallic layer to produce a plurality of metallized microtower electrodes; depositing a biocompatible laminate layer on the plurality of metallized microtower electrodes, micromachining a plurality of apertures into the biocompatible laminate layer, wherein each of the apertures is arranged to correspond with the tip of one of the plurality of metallized microtower electrodes; and electrospinning an electrospinning solution to form a plurality of interconnected nano-scaffolds in a three-dimensional pattern above the tip of each of the plurality of metallized microtower electrodes. The metallic layer may comprise a metal selected from titanium, gold, and combinations thereof. The metallic layer may have a thickness of from about 10 nm to about 100 nm. The biocompatible laminate layer may include an adhesive. In a specific embodiment, the micromachining step occurs prior to depositing the biocompatible laminate layer on the layer of the metallic compound.

The method for producing a microelectrode platform may further involve functionalizing the plurality of interconnected nano-scaffolds by incorporating a bioactive agent (as discussed above) into the electrospinning solution.

A further method pertains to biosensing using a microelectrode platform as described herein. The biosensing method involves disposing a biological sample in a microelectrode platform and detecting an impedance between the metallized microtower electrodes.

Another method pertains to delivering an agent in a biological sample that involves disposing the biological sample in a microelectrode platform having nanoscaffolds embedded with a bioactive agent as described herein and allowing the one or more bioactive agents to be released such that they contact the biological sample.

Overview

MEA technology is a highly popular and widely used platform for recording and stimulating electrical activity in electrogenic cells such as neurons, cardiomyocytes, pancreatic beta cells etc. for both in vitro and in vivo applications

[10]. A MEA platform can additionally be used to study the electrical activity of coordinated bacterial behavior during formation of bacterial biofilms [11]. Microfabrication technologies are apt for realizing MEAs and they have primarily been realized with silicon microassembly or complex monolithic microfabrication-based approaches [12]. This however restricts monolithic MEAs to be two-dimensional (2D) since lithographic techniques on non-planar surfaces is particularly challenging [13], [14]. Although previous studies have developed intricate techniques to fabricate 3D microelectrode nanoprotrusions [15] or mushroom-type structures [16], they are all limited in the height to which the cellular network can be studied in 3D, which are typically ~1 µm in Z-axis [15], [16]. Absence of or severely limited 3D functionality in MEAs without complex processes makes them inadequate to capture signals or perform therapeutic functions that occur at a certain height when cultures mature to obtain a 3D form.

Additive manufacturing has recently shown the potential to transform microengineering with its ability to realize true 3D structures monolithically with rapid single step translations. Such additive manufacturing involves a layer by layer construction of the designed 3D geometry using a 3D printer. Among the various 3D printing technologies, microstereolithography (µSLA) based 3D printing provides a balance between the print resolution, print time, build volume and cost. SLA 3D printers are inexpensive, benchtop systems typically found in makerspaces, which are providing a growing alternative to cleanrooms for realization of nanobiosensors, biomedical micro-electro-mechanical systems (BioMEMS) and micrototal analysis systems (MicroTAS) [17]. The concept of 'Makerspace Microfabrication' [17] has been recently introduced, which was used for the realization of biological microdevices such as 2D Microelectrode Arrays (MEAs), microneedles (MNs) and Microfluidic Channels (MFCs). Specifically, the process described in earlier work was enabled by 3D printing, Ink Casting, Lamination and Micromachining and involved a close synergy between the additive and subtractive micromachining processes. The process described was hierarchical in nature with each subsequent process building upon the functionality provided by the preceding procedure. Due to the highly flexible and adaptive nature of 'Makerspace Microfabrication,' new processes offering advanced functionalities can be added to the toolbox in order to realize other biological microdevices such as 3D MEAs. The integration of benchtop processes such as electrospinning could address the requirements of 3D ECM. Electrospinning is a fiber fabrication technique that employs electrostatic charges to produce fibers that can range from 2 nm to several µm in diameter based on the fabrication optimization [18].

Figure 14:
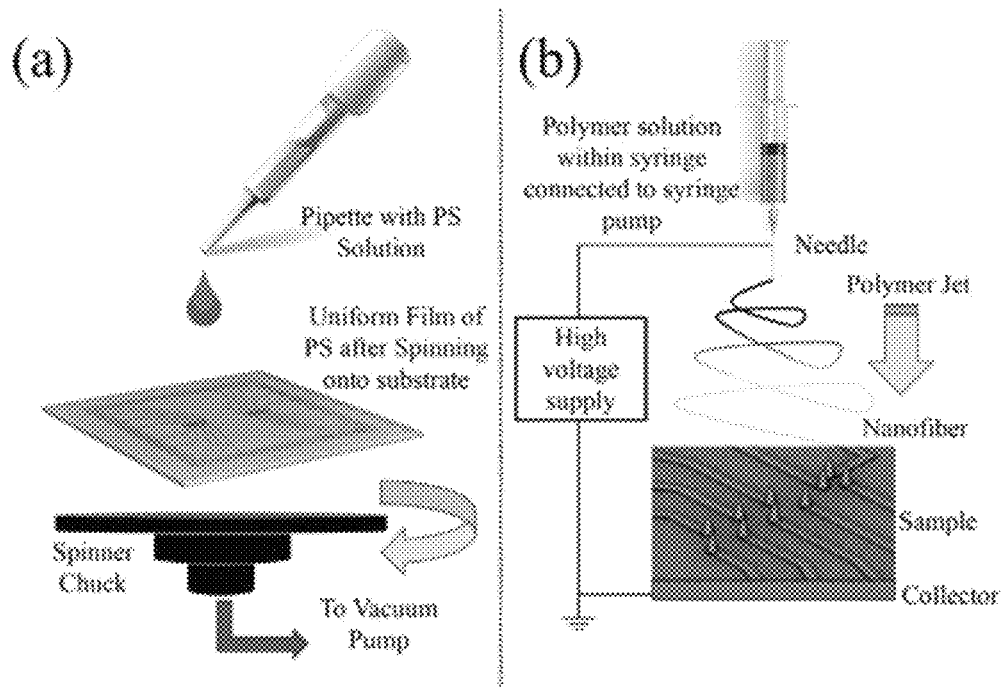
FIG. 14: (a) Schematic of the drop-casting and (b) electrospinning techniques, both on 3D microtower arrays.

Electrospinning is an attractive method for nanofiber fabrication because it has several advantages, such as versatility, cost effectiveness, ease of use, and ability to control fiber diameters [19]. This technique utilizes an electric field to produce a polymer jet from a solution [18], [20]. The polymer jet is formed when the surface tension of the solution is surpassed by the applied electrostatic charge. FIG. 14 shows the schematics of the drop-casting/spin-coating and electrospinning processes, respectively.

This jet dries during flight towards the grounded collector and is elongated by electrostatic repulsion with nearby segments of the same jet. By the time the jet reaches the collector, the solvent has evaporated and the jet solidifies into a nanofiber. Critical parameters such as the polymer of interest's molecular weight, concentration of polymer, solution properties, electrical potential between the needle and the collector, flow rate of the solution, the needle gauge and distance between the needle and the collector need to be optimized in order to achieve nanofibers with specific properties. Recent work has demonstrated that the deposition of electrospun nanofibers on top of 3D structures depends on the aforementioned processing parameters [21]. Thus, a synthetic ECM, or scaffold, can be realized by exploiting the electrospinning technique to address the mismatch problem between cells and the interfacing device.

By optimizing the chemical composition of the material solution, electrospinning parameters and post processing of the nanofibers, a scaffold can be customized for a specific tissue, making this technique very versatile for multi-functional cell-based sensors. Another advantage of nanofibers is the possibility of loading the fibers with various molecules such as drugs, proteins, toxins and metal ions [22]-[27]. Specifically, silver nanoparticles have been shown to demonstrate potent antimicrobial properties [28]-[30]. Two types of polymeric solutions: polyethylene terephthalate (PET), and a copolymer blend of poly (acrylic) acid (PAA) and poly vinyl alcohol (PVA) are of particular interest due to their unique properties. PET is a hydrophobic polymer that is conventionally found in prosthetic vascular grafts due to its biocompatibility and mechanical endurance/strength [31]. It has additionally been demonstrated that fibrous PET scaffolds for human Mesenchymal Stem Cells (hMSCs) culturing provide high surface area, high porosity and permeability, excellent mechanical strength, and good thermal and chemical stability [31], [32]. Furthermore, a polyelectrolyte blend of PAA and PVA is also used to fabricate the fibrous scaffolds. PAA is a biocompatible hydrophilic polymer that is easily ionizable due to its carboxyl groups and thus provides a swelling behavior to the fibers [33]. PVA is a nontoxic and biocompatible hydrophilic polymer with advantageous properties such as improved mechanical strength, gas permeability, water solubility and thermal stability [34]. PAA and PVA are oppositely-charged hydrophilic polyelectrolytes in which polyelectrolyte complexes are formed and used to improve the stability of fibers [25].

The realization of a suitable spin coated insulation layer for such 3D electrodes has always remained a challenge due to diverse topographies for conformal deposition of biocompatible materials with a low thermal budget. Spray, dip, conformal vapor and electroplated resists have been used for 3D coatings but do require specialized instrumentation (e.g. expensive 3D spray coaters) or processes unsuitable for polymer microfabrication [35]-[39]. Selective removal of the insulation layer from the top of the metallized 3D geometry also allows for the definition of electrodes typically down to 50×50 µm2 [40]. Conventionally used photoresists such as biocompatible SU-8 do not perform well for 3D geometries with high topography because of their high viscosities. The challenge is to adjust the evaporation rate and the solid content of the photoresist which may be achieved with the help of solvents such as methyl-ethyl ketone (MEK) and propylene glycol monomethyl ether acetate (PGMEA) [41]. Although the dilution makes the photoresist solution more mobile, it also makes the coating very non-uniform in 3D topographical regions. This also results in accumulation of the photoresist along the bottom surfaces having the 3D topography. Thus, both the 3D geometry and the planar surface housing the 3D geometry suffer from either poor coverage or lumped coatings of the photoresist respectively. The key to achieving conformal coatings on 3D structures having high aspect ratios is to engineer the balance between the viscosity of the solution and its evaporation rate. An optimum viscosity will allow for mobility to coat 3D geometries whereas the optimum solvent evaporation rate would prevent any unwanted accumulation of the material being spin coated.

In recent years, the use of liquid polystyrene (PS) as a room temperature, photocurable, soft lithography technique compatible with "pour-and-cure"-type processes have received much interest [42]. By tuning the solid content of the PS mixture, we can control the thickness of the coating and by altering the liquid content and type of solvent we can regulate the evaporation rate of the mixture, thus realizing a onestep 3D insulation layer. This pour-spin-and-cure insulation defining technique is another toolbox process added to makerspacemicrofabrication.

Disclosed herein are techniques and systems that implement 3D printing toward the microfabrication of in vitro 3D MEAs. The metallization of the 3D printed parts has been performed by standard physical vapor deposition techniques through a micromilled stencil mask. Insulation of the metal traces with a biocompatible laminate layer results in the 3D microtower electrodes. Full spectrum impedance analysis of the fabricated microtower electrodes confirms meso-scale electrode behavior. Also disclosed is the integration of a synthetic ECM, by utilizing electrospun nanofibers, atop the 3D MEAs. The 3D Nano Fiber Scaffolds (NFS) are electrospun from two types of polymeric solutions: polyethylene terephthalate (PET), and a co-polymer blend of poly (acrylic) acid (PAA) and poly vinyl alcohol (PVA). The nanofiber mats were characterized by contact angle studies to determine the wettability of the scaffolding, Fourier Transform Infrared Spectroscopy (FTIR) to confirm the composition of the material and Scanning Electron Microscopy (SEM) to determine the morphology of the fiber network. To demonstrate the versatility of nanofibers beyond applications as scaffolds for 3D MEAs, the electrospun PVA/PAA nanofibers were functionalized with silver nanoparticles (Ag NPs).

As provided in the Examples below, the results demonstrate the potential of the scaffolds in vitro drug delivery, where Ag NPs was the model drug and the effectiveness as a bactericide was determined by a simple zone of inhibition study. The characterization of the Ag NPs functionalization was accomplished through Transmission Electron Microscopy (TEM) and bacterial studies to examine the antibacterial properties of the functionalized polymer nanofibers. Finally, a 3D insulation strategy was demonstrated involving drop-casting and spincoating of Polystyrene (PS), which was subsequently laser micromachined to realize the microelectrode recording sites (50×50 µm2 area) on the 3D MEA. The 3D insulation technique followed by laser micromachining transforms the meso-scale 3D microtowers to the microscale 3D MEAs. FTIR confirms the PS layer in 3D and SEM imaging was performed to demonstrate the geometry of the 3D MEAs, the conformal deposition of the PS insulating layer and laser ablation parameters. Electrical Impedance Spectroscopy (EIS) measurements were performed to confirm typical MEA behavior.

Example 1: Materials and Methods

A. Fabrication of 3D Microtower Electrodes

The 3D microtower electrodes were designed in Solidworks (2016×64 bit edition, Dassault Systems Inc., Waltham, MA, USA). The MEA chip has a size of 49 mm×49 mm×1 mm to ensure connectivity with the Multi-Channel Systems (Reutlingen, Aspenhaustrasse, Germany) recording amplifiers. Two patches, each containing ten recording sites in the form of 3D towers was designed. The microtowers had a base diameter of 250 µm and a height of 400 µm with a 600 µm pitch. The designed CAD file was directly printed in a 3D SLA printer Form Labs Form 2 (Somerville, MA, USA) with a laser wavelength of 405 nm using a photopolymer clear resin (FLGPCL04, Formlabs, Somerville, MA, USA) with an ultimate tensile strength (UTS) of 65 MPa [43]. The devices were thoroughly rinsed twice with isopropyl alcohol (Sigma-Aldrich, St. Louis, MO, USA] for 10 minutes and carefully dried with aid of a nitrogen gun. Prior to metallization, oxygen plasma treatment using PE Plasma Cleaning System [Plasma Etch, Carson City, Nevada, USA] was performed for 5 minutes at a power of 30 W with an oxygen gas flow rate of 5 sccm. The metallization of the 3D microtowers and definition of the traces (200 µm wide) were performed by deposition through a stencil mask. The stencil mask was aligned with the 3D printed substrate under a stereoscope and affixed together with the aid of 1 mil (25 µm) polyimide, high temperature Kapton® tape. For the fabrication of the stencil mask, a 90-degree T-8 Mill Tool (150 µm-250 µm diameter; T-Tech, Peachtree Corners, GA, USA) was spun at 55,000 rpm in a T-Tech QC-J5 Quick Circuit Prototyping Systems to cut into a stainless steel sheet (80 µm thick; Trinity Brand Industries, Countryside, IL, USA). In order to define the metallization layer, titanium (Ti, 4N5 purity pellets) and gold (Au, 5N purity pellets) [Kurt J. Lesker, Jefferson Hills, Pennsylvania, USA] were deposited by electron-beam (E-beam) evaporation [Thermionics Laboratory Inc., Hayward, California, USA]. The Ti and Au layers were deposited at a vacuum of 3.1×10−6 Torr with layer thicknesses and deposition rates of: 10 nm layer and 1.0 nm/s for Ti and 100 nm at 1.0 nm/s for Au respectively. A biocompatible laminate layer (Medco® RTS3851-17 adhesives ~50 µm thick plus Poly Ethylene Terephthalate (PET) ~20 µm thick; Medco Coated Products, Cleveland, OH, USA) is subsequently laminated to the 3D printed chip to insulate the traces thereby enabling the realization of a 3D microtower electrodes having a size of the entire 3D printed structure. The biocompatible laminate is additionally micromilled prior to its alignment and attachment to have openings corresponding to the size of the two patches of 3D tower arrays, each containing ten recording sites. A culture well having an inner diameter of 30 mm is 3D printed, coated with Poly Dimethyl Siloxane (PDMS) to enhance biocompatibility and bonded using a biocompatible adhesive (Epo-tek® 353ND) to realize the final device. FIG. 1 depicts an exploded view of the components of the 3D microtower electrodes along with close-up schematic of the ten recording sites in a single patch.

B. PET Nanofiber Fabrication

The Polyethylene Terephthalate (PET) solution was composed of 20% (w/w) PET (Sigma Aldrich, St. Louis, MO, USA) dissolved in a mixture of trifluoroacetic acid (TFA) (Thermo Fisher Scientific, Waltham, MA, USA) and dichloromethane (DCM) (Thermo Fisher Scientific, Waltham, MA, USA) having a TFA:DCM volume ratio of 70:30. Electrospinning of PET was performed using a working distance of 12 cm, an applied voltage of 10 kV and a flow rate of 99 µL/hr.

C. PVA/PAA Nanofiber Fabrication

Poly (vinyl alcohol) solutions were composed of 10% (w/w) PVA (Sigma Aldrich, St. Louis, MO, USA) and prepared by dissolving PVA (99+% hydrolyzed, Mw 89,000-98,000) powder in distilled water. In order to dissolve the solution, water was preheated to 80° C. and magnetic stirring was applied for 4 hours until the solution was fully dissolved. PVA would subsequently be mixed with PAA partial sodium salt solution (25 wt % in H2O, average Mw ~240,000 by GPC) (PAA) (Sigma Aldrich, St. Louis, MO, USA). Once the PVA solution was fully dissolved, the PVA and PAA solutions were mixed in a 1:2.5 mass ratio and placed under magnetic stirring for 30 minutes prior to electrospinning. The process of electrospinning of PVA/PAA was performed at a working distance of 20 cm, an applied voltage of 16.2 kV and a flow rate of 2 μL/hr. Thermal crosslinking of PVA/PAA prevents dissolution of the nanofiber mats in solution. After testing different temperatures and times, a 145° C. for 30 minutes crosslinking step was applied that resulted in no dissolution of the nanofiber mats.

D. Functionalization of PVA/PAA Nanofiber Mats

Functionalization of the nanofiber mats was accomplished through the incorporation of silver into the PVA/PAA electrospinning solution. A solution of silver nitrate ($AgNO_3$) was prepared by dissolving crystalline silver nitrate (Fisher Chemical, Waltham, MA, USA) into nanopure water to make a 0.10 M $AgNO_3$ solution. Silver nitrate was added in excess in order to ensure proper functionalization.

After electrospinning and heat treatment of the mats, the nanofiber mats containing silver were reduced using a sodium borohydride ($NaBH_4$) solution. A 0.01 M sodium borohydride solution was prepared by dissolving sodium borohydride pellets (98% min, Alfa Aesar, Haverhill, MA, USA) into nanopure water. PVA/PAA nanofibers were exposed to $NaBH_4$ solution for 1 minute, followed by the removal of the solution and the exposed nanofibers were rinsed with distilled water.

E. Fiber Morphology Studies

In order to study the fiber morphology, nanofibers were electrospun into mats and imaged using Scanning Electron Microscopy (SEM; Carl Zeiss ULTRA-55 FEG SEM, Birkerod, Denmark). SEM also aided in observing the interaction of electrospun nanofibers atop the 3D printed MEAs. Transmission Electron Microscopy (TEM; JEOL TEM-1001, Peabody, MA, USA) was employed to determine the distribution and size of the Ag nanoparticles (NP) embedded within the PVA/PAA nanofibers.

F. Contact Angle Measurements

Contact angle studies were conducted using an OCA 15EC contact angle measurement device (DataPhysics Instruments GmbH, Filderstadt, Germany). Contact angle studies were performed for the following samples: PET, PVA/PAA before thermal crosslinking, and PVA/PAA after thermal crosslinking. Four different fiber densities of PVA/PAA after thermal crosslinking were measured. The four samples differed in the electrospinning time to vary the fiber density, and included mats that were electrospun for 30 minutes, 1 hour, 1.5 hours, and 2 hours.

G. Bacterial Studies

The antibacterial properties of the silver-functionalized PVA/PAA nanofiber mats were characterized as proof of concept toward the multifunctional biosystems, using two strains of bacteria via the disc diffusion method. The procedure used for this testing was followed according to that detailed by Bauer et al. [44]. The bacteria used for this study were *Acinetobacter baumannii* (ATCC19606) and *Escherichia coli* (ATCC10798). The bacterial culture was diluted to a 0.5 McFarland standard and subsequently used to lawn agar plates to achieve confluent growth of bacteria spread evenly over the plate. Once the nanofiber mats were placed in the center of the culture dish, the plates were incubated at 37° C. for 24 hours. After 24 hours, the zone of inhibition was measured and analyzed with ImageJ (National Institute of Health, Bethesda, MD, USA), using the ruler in the pictures as a scale.

H. 3D Insulation Layer Definition and Realization of 50×50 $\mu m^2$ MEA

Figure 2:
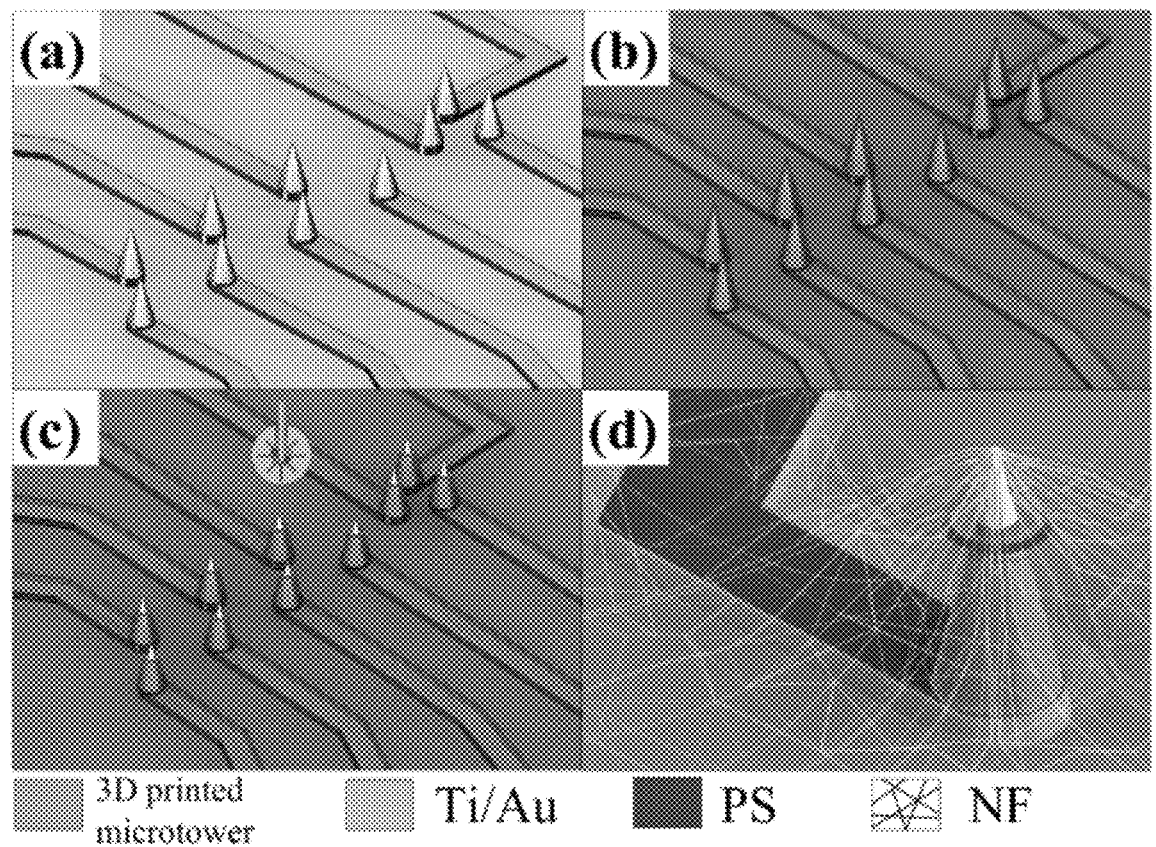
FIG. 2: Schematic of the 3D insulation and nanoscaffolding process flow—(a) Metallized 3D towers; (b) 3D PS insulation atop the metallized 3D towers; (c) Insulation ablation using a laser micromachining process (Laser symbol in green); (d) PET or PVA/PAA nanofiber scaffold (NFS) deposited on the insulated, laser ablated, 3D MEA by electrospinning.

To realize smaller electrodes, a polystyrene (PS) insulation layer is defined atop the 3D microtowers [FIG. 2(a): before insulation and FIG. 2(b): after insulation]. FIG. 1 depicts an exploded view of the components of the 3D microtower electrodes along with close-up schematic of the ten recording sites in a single patch. The PS solid (~280 kDa, Sigma Aldrich, St. Louis, MO, USA) was dissolved in tetrahydrofuran (THF) (Thermo Fisher Scientific, Waltham, MA, USA). Concentrations consisting of 10%, 20%, 30% and 40% PS in THF were prepared to determine the optimal concentration and spinspeeds to achieve an insulation thickness of approximately 5 μm comparable with commercial 2D MEAs [45] and other polymer 3D MEAs approaches [46]. The insulation layer was achieved by either a drop-casting or drop-casting/spin-coating technique using PS. To evaluate the performance of the drop-casting technique, 2 mL of aforementioned concentrations of various PS solutions were dispensed first onto glass slides. To insulate the 3D microtower using the dropcasting technique, 2 mL of 10% PS was dispensed to fully envelop the microtower device and allowed to sit at room temperature for the solvent to evaporate to leave behind a thin film layer. For the dropcasting/spin-coating technique, the insulation layer was dispensed in a similar fashion on glass slides. The slides were immediately spun before the solvent could evaporate. Spin-coating at 500 rpm, 1000 rpm and 5000 rpm were performed for 30 seconds and the resulting film thickness was measured using a profilometer (AlphaStep D-500 Stylus Profiler, KLA-Tencor, Milpitas, CA, USA). Once the planar glass slides were characterized, a 30% PS solution was chosen and spincasted on 3D printed microtowers of the following heights: 1200 μm, 1600 μm and 2000 μm (all devices fabricated with aspect ratios of 2), at 1000 rpm for 30 seconds. The thickness of the 3D PS insulation layer was determined from scanning electron microscopy (SEM) images by carefully cleaving the towers prior to SEM and measuring film thickness near the tips of the towers with the aid of ImageJ. The translation of film thickness from planar to three-dimension was validated by this study. Thus, to obtain a desired thickness of 5 μm on a 3D structure, 20% PS solution drop-casted and spin-coated at 5000 rpm for 30 seconds was chosen based on the 2D data. Prior to the spincoating, a culture well with an inner diameter of 30 mm is 3D printed, coated with Poly Dimethyl Siloxane (PDMS) and bonded to the microtower array using a biocompatible adhesive (Epo-tek® 353ND) to realize the final device. The 3D insulation layer could subsequently be selectively ablated by laser micromachining to defined 3D microelectrodes [FIG. 2 (c); microelectrodes: 50×50 μm2; a 532 nm laser beam at an energy level of 1.2 mJ] utilizing QuickLaze 50ST2 (Eolite Lasers, Portland, OR, USA). SEM was used to characterize the microelectrodes. FIG. 2 (d) shows a schematic representation of an electrospun NFS that can be optionally performed atop the PS insulated, laser micromachined MEA.

I. Fourier-Transform Infrared Spectroscopy

Fourier-Transform infrared spectroscopy (FTIR) was performed for the PS insulation layer, PET anofibers, along with the various PVA/PAA nanofibers. FTIR measurements were conducted using a PerkinElmer Spectrum 100 FT-IR Spectrometer (Waltham, MA, USA) where 1-5 mg of sample was used for each FTIR trial.

J. Electrical Characterization of 3D Microtower MEAs Throughout Various Steps of Device Fabrication Impedance measurements of the MEAs were performed with the 3D MEAs at the various stages: microtowers, 3D microelectrodes, with and without nanofibers using Bode 100 (Omicron Labs, Houston, TX, USA) with Dulbecco's Phosphate Buffer Solution (Thermo Fisher Scientific, Waltham, MA, USA) as the electrolyte. The impedance scans were carried out from 10 Hz to 1 MHz with a platinum wire (eDAQ, Denistone East, Australia) as the counter electrode.

Example 2: Fabrication of 3D Microtower MEAs

Figure 3:
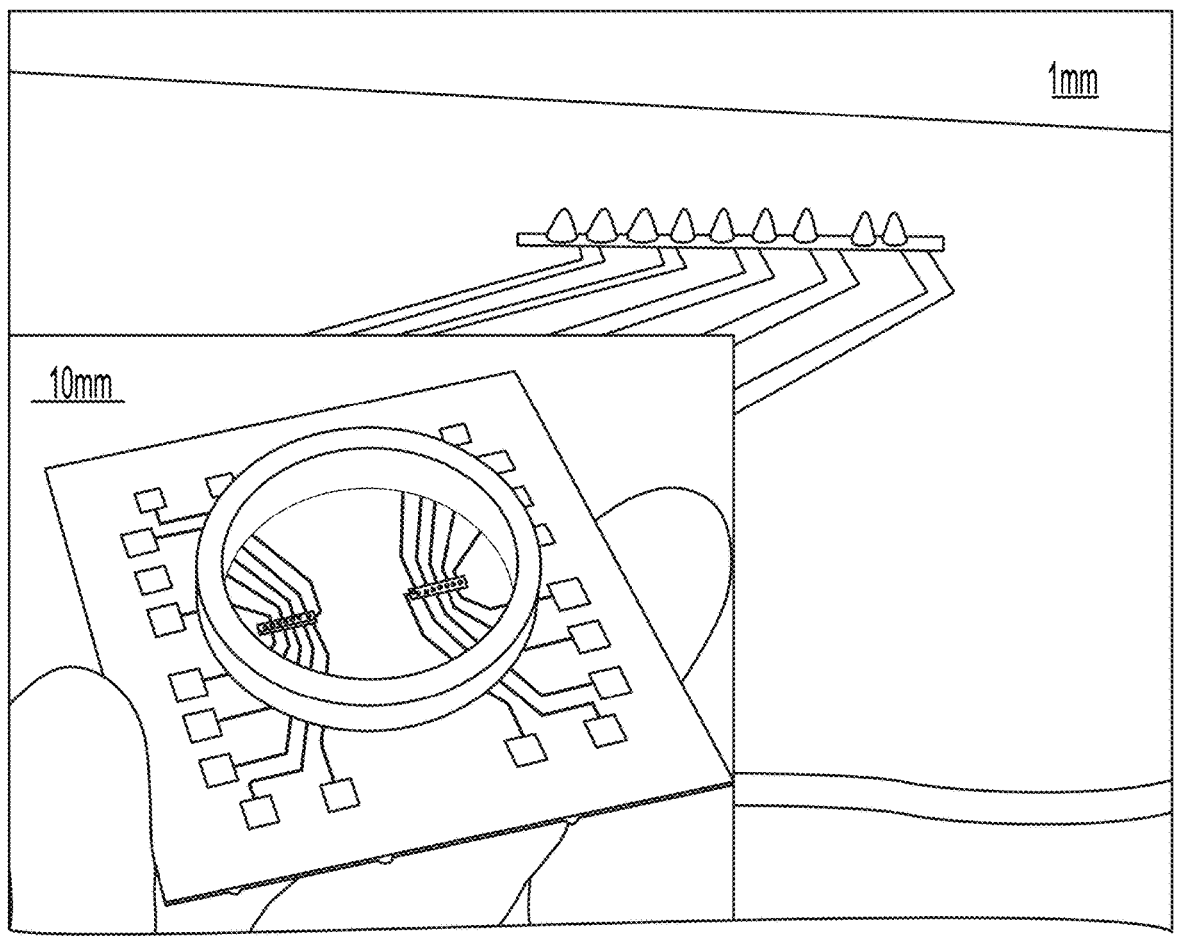
FIG. 3: Optical micrographs of the 3D microtower MEA with the final, packaged device shown in the inset.

FIG. 3 depicts the optical micrographs of routed, metallized microtowers with the packaged 3D MEAs depicted in the inset. At this stage the entire 3D printed tower is metallized and the size of the microelectrode corresponds to that of the 3D printed tower (base diameter: 250 µm and height: 400 µm). The biocompatible transparent laminate layer protects the traces from any culture/electrolyte solution contained in the culture well and as a result from shorting. SEM imaging of the 3D printed microtowers were performed (N=20) to find the design to device translation metrics. The mean base diameter was measured to be 249.3 µm with the minimum and maximum printed dimensions being about 240 µm and about 260 µm respectively. Additionally, the mean height was calculated as 400.35 µm with the minimum and maximum printed dimensions being 390 µm and 410 µm respectively. Thus, it is observed that the microtower dimension closely matches the design dimension of 250 µm base diameter and 400 µm height.

Example 3: Scaffolding of 3D Microtowers: Optimization and Characterization

Figure 4:
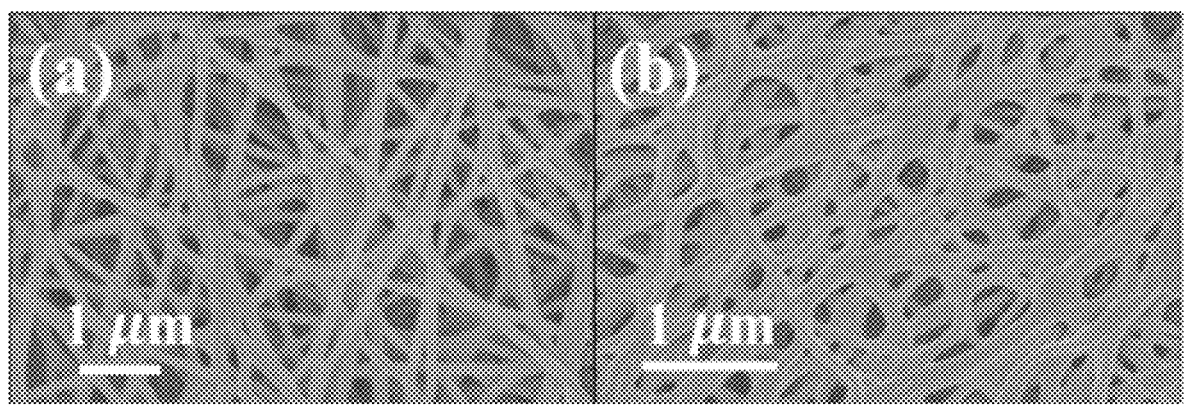
FIG. 4: SEM images of PVA/PAA nanofibers electrospun onto a planar substrate (a) before heat treatment and (b) after heat treatment.

PET-NFS are ready to be used as a scaffold immediately after electrospinning due to the inertness to aqueous media such as saline solution. However, PVA/PAA-NFS have to be crosslinked to prevent the dissolution in aqueous media since the fibers are highly soluble in water. Crosslinking is achieved by heat treatment of the fibers and occurs via a dehydration, reaction where the alcohol group of PVA and the carboxylic group of PAA react to form an ester, simultaneously releasing water. FIG. 4 provides SEM images of PVA/PAA nanofibers before and after heat treatment. It can be observed in FIG. 4 (b) that heat treatment resulted in curved morphologies, fusing of nanofibers and a decrease in interfiber spacing as compared to FIG. 4 (a). Fusing was observed between adjacent fibers since crosslinking occurred at the point of contact. The fibers in FIG. 4 (b) compared to FIG. 4 (a) additionally appear to be larger for the same reason, the crosslinking and fusing along the length of the fibers increased the diameter of the fibers. Consequently, fusing resulted in decreased interfiber spacing, which gives rise to bulk properties of the fiber networks. Interfiber spacing of nanofibers is an important property that is dictated by the application. Qualitatively, the heat treated PVA/PAA nanofibers resulted in rigid and water-resistant mats optimized to be deposited on fully packaged 3D microtowers.

Figure 5:
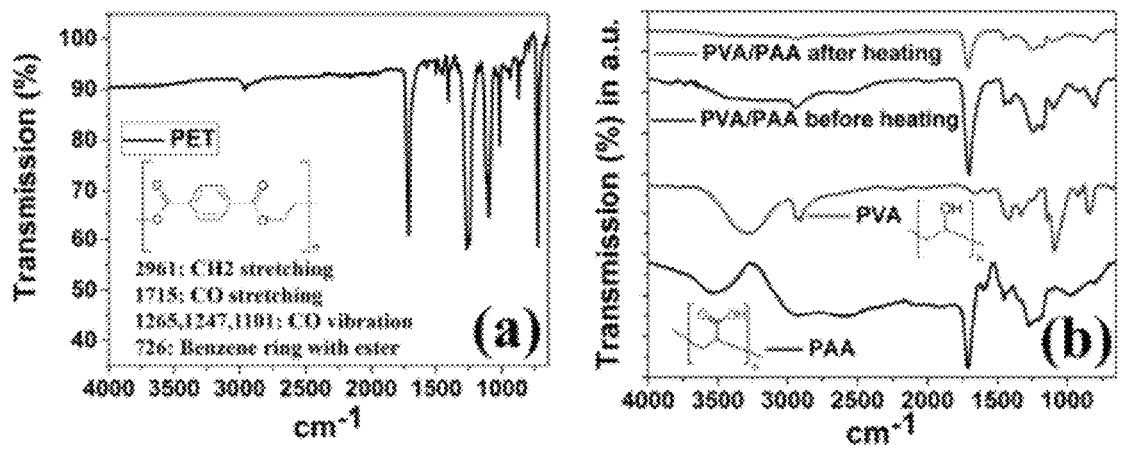
FIG. 5: FTIR analysis of (a) electrospun PET and (b) PVA, PAA, and an electrospun mat of PVA/PAA before and after heat treatment.

FIG. 5 (a) provides the FTIR results for the electrospun PET with a noteworthy peak for PET at 726 cm-1, which derives from the benzene ring's interaction with polar ester groups. The C—O peaks at 1265 cm-1, 1247 cm-1 peak and 1101 cm-1 and the very prominent carbonyl peak at 1715 cm-1, confirm the presence of the ester groups from PET. Finally, the peak at 2961 cm-1 helps confirm the presence of a methylene group to suggest that the molecule is PET. FIG. 5 (b) illustrates four separate FTIR spectra: powdered PVA, PAA solution, and a PVA/PAA nanofiber mat before and after heat treatment. The peaks and stretching of interest that are examined in this figure are the broad alcohol group stretching that occurs between 3500-3000 cm-1 and the carbonyl peak that occurs around 1700 cm-1. As seen in FIG. 5 (b), PVA displays the characteristic alcohol peak and PAA displays the carbonyl peak. The nanofiber mat containing both PVA and PAA before heat treatment displays both of these characteristic peaks. One of the interesting trends to examine is the effect that heat treatment has on the PVA/PAA nanofiber mat. After heat treatment, there was a disappearance of the alcohol peak and a shift in the carbonyl peak from 1703 cm-1 to 1709 cm-1. These changes are both indicative of crosslinking in which an alcohol and carboxylic acid are converted into an ester.

Figure 6:
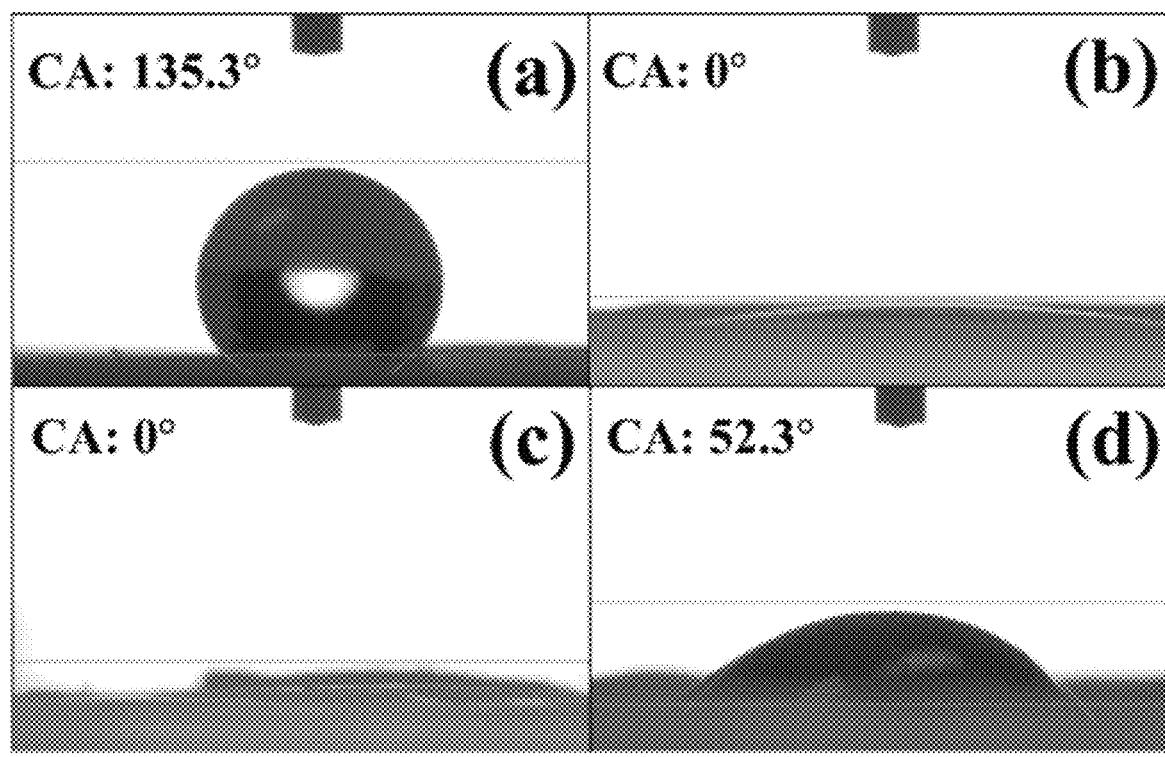
FIG. 6: Contact angle (CA) imaging results: (a) PET and PVA/PAA (b) before heat treatment, (c) after heat treatment in an area of the mat with a lower fiber density, and (d) after heat treatment in an area of the mat with a higher fiber density.

Contact angles (CA) of PET and PVA/PAA from different conditions were measured and are depicted in FIG. 6. CA measurements are conducted to examine the wettability of a surface and the hydrophobic/hydrophilic properties of the nanofibers. In most cases, a contact angle above 90° indicates a hydrophobic surface, while a contact angle below 90° indicates a hydrophilic surface [29]. The CA of a PET was 135.3° [FIG. 6 (a)], which was as expected due to the hydrophobic nature of the material [48]. The CA for PVA/PAA before FIG. 6 (b)] and after [FIG. 6 (d)] crosslinking was the same and measured to be 0°. When the water droplet was placed onto the noncrosslinked PVA/PAA mat for CA determination, the mat was immediately dissolved. This indicates an extremely hydrophilic surface, consequently unstable in solution. Crosslinking addressed this issue by making the material less hydrophilic with the formation of ester bonds. Although, the measured CA for the crosslinked mat, spun for 30 minutes, was measured to be 0°, it did not dissolve like the untreated mat did. At a longer electrospinning time of 1 hour, the CA angle measurement increased to 52.3° as depicted in FIG. 6 (d). Electrospinning time determined the thickness and consequently the surface roughness and interfiber spacing. As the amount of fibers collected, or thickness, decreases, the amount of interfiber spacing increases. As the amount of interfiber spacing increases, the ability of the water to disperse within the fiber mesh also increases, resulting in a lower contact angle. Additional studies on the effect of nanofiber density as a function of electrospinning time were performed for 1.5 hours and 2 hours and resulted in similar contact angles of 52.3°, which was obtained for 1 hour of electrospinning. This study indicates that interfiber spacing is not affected by electrospinning time beyond 1 hour. However, additional testing is necessary to determine the exact correlation between the interfiber spacing, surface roughness and contact angle.

Figure 7:
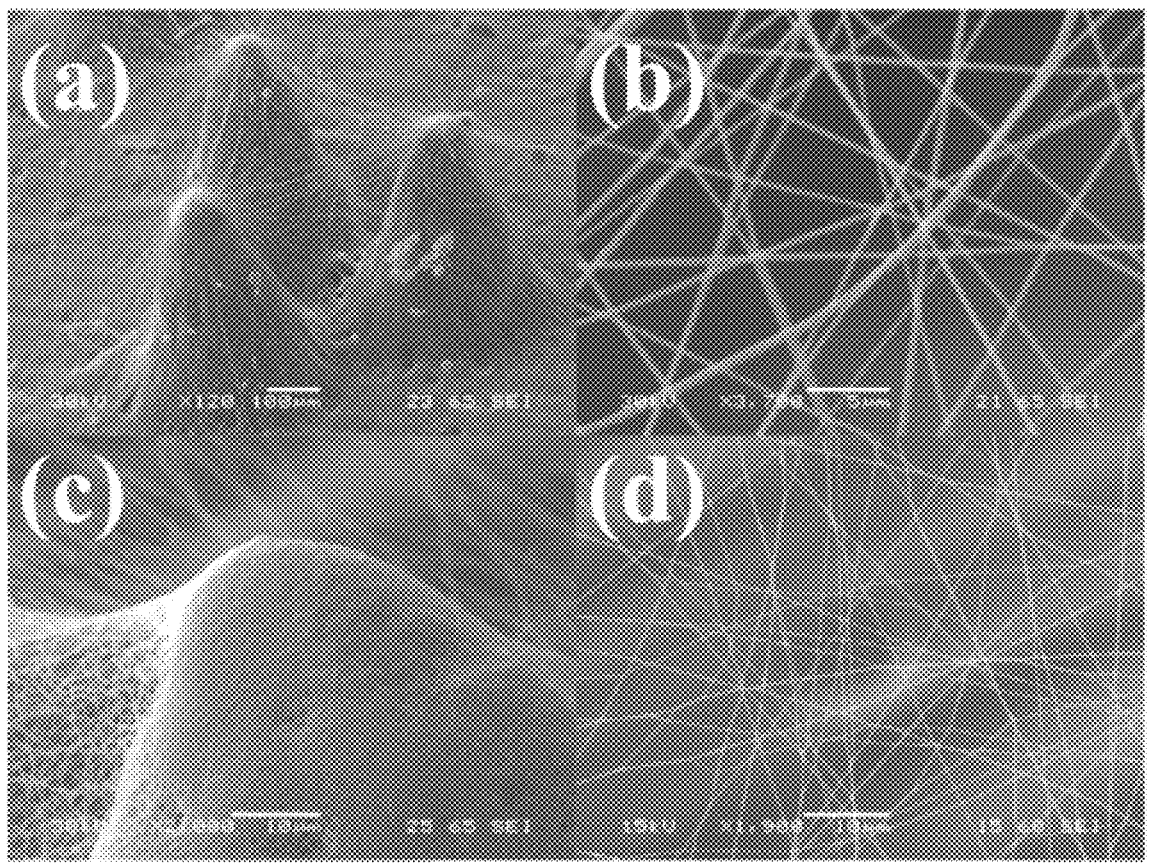
FIG. 7: SEM images of 3D MEA microtowers with electrospun (a) PET-NFS with a (b) close-up view of the PET-NFS showing fiber widths of ~200-500 nm and (b) 3D MEA microtowers with PVA/PAA-NFS and (d) close-up view of the PVA/PA-NFS showing fiber widths of ~100 nm.

FIG. 7 (a) shows the SEM image of 3D PET nanofiber scaffold (PET-NFS) deposited atop the 3D MEA. It is clearly seen that the nanofibers interlink between the 3D electrodes providing effective scaffolding. FIG. 7 (b) depicts a close-up image of the PET-NFS with a fiber width of ~200-500 nm. FIG. 7 (c) depicts the SEM image of PVA/PAA nanofiber scaffold (PVA/PAA-NFS) atop the 3D MEA. A close-up of the PVA/PAA-NFS is provided in FIG. 7 (d) with average fiber widths of ~100 nm. An important factor to take into consideration when fabricating a suitable scaffold material is the morphology and networking of the fibers produced, as this will have an effect on the functionalized biomedical system for instance in vitro cell culture systems. The PVA/PAA-NFS display several beneficial properties for application as cell culture scaffolding such as the lack of beading, uniformity of fiber width and the use of non-toxic solvents for polymer solution prior to electrospinning. PET-NFS contained beading shown in FIG. 7 (a) and a larger range in widths as can be seen in FIG. 7(b). In addition, PET electrospinning solution is composed of TFA and DCM which are toxic and difficult to handle. Therefore, residual solvent left in or on nanofibers and beads could be detrimental to cells. For these reasons, further experiments were carried out only with PVA/PAA-NFS.

An interesting observation was the slight radial alignment of fibers extending from the tip of the microtower out [FIG. 7 (a)]. Previous studies have reported similarly aligned nanofibers made out of collagen used for tendon regeneration [49]. Within that study, the authors observed that radial alignment of the scaffold served as a guide for the fibroblasts to spread along, towards the center of the scaffold. The unique alignment of the nanofibers due to the attraction to the metalized tip of the 3D microtower creates a few advantages as cellculture monitoring platforms. For instance, cells spreading along the fibers as they grow near the electrode and motility towards the center of the scaffold increases cell-electrode coupling and the growth of cells along the scaffold can prevent dead cell layers.

When depositing nanofibers on top of the 3D microtowers, it is important to consider how much is deposited. FIG. 7 (c) depicts PVA/PAA NFS deposited for 1 hour, which resulted in a very dense collection of fiber mat on top of the electrode. However, the density and number of nanofibers deposited can be controlled by varying the time of electrospinning.

Figure 8:
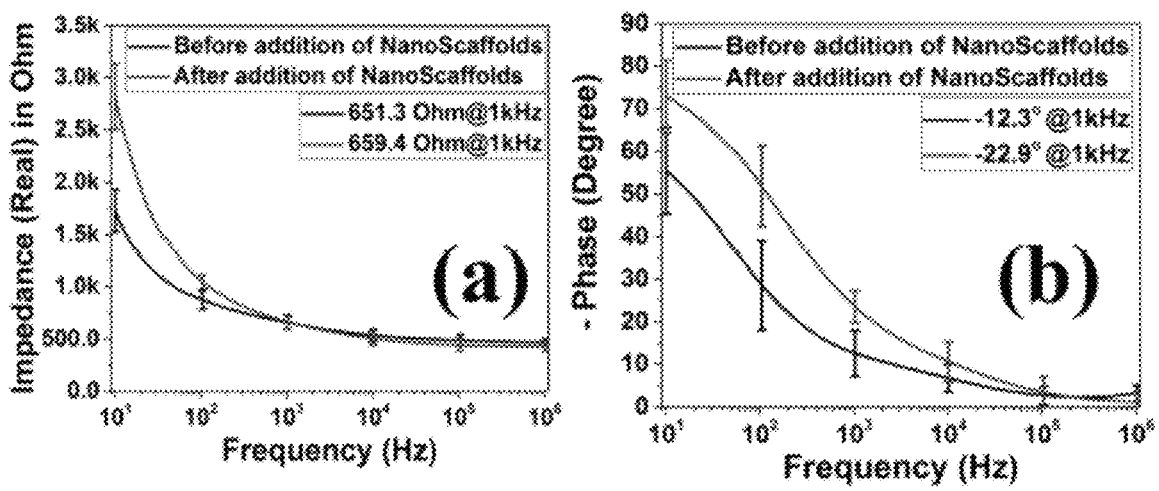
FIG. 8: Electrical Impedance Spectroscopy (EIS) Plots of the (a) real and (b) phase portions of complex impedance for the large area microtower (N=4) 3D MEAs with and without PVA/PAA NFS.

FIGS. 8 (a) and (b) depict the full spectrum impedance (N=4) and phase response of the 3D microtower electrodes before and after addition of PVA/PAA NFS with electrospinning for 30 minutes. It is observed that the magnitude of impedance in the low frequency region (<100 Hz) increases upon addition of the NFS. This can be attributed to the increased obstruction caused by the NFS at the electrode/electrolyte interface leading to an increase in the charge transfer resistance (RT). However, at the electrophysiologically significant frequency of 1 kHz, the impedance remained unchanged (651.3Ω before and 659.4Ω after NFS integration). As depicted in the error bars of FIG. 8 (a) indicates a tight statistical distribution of the impedance demonstrating reproducibility of the process. The phase spectrum is observed to shift from −75° to nearly 0° and −55° to nearly 0° for the 3D microtowers with and without the NFS respectively. This implies that the overall characteristics of the electrode-electrolyte interface in both cases is governed by the double layer capacitance (CDL) at the mid-frequency band and becomes more resistive at high frequencies as the solution resistance of the electrolyte begins to dominate the electrode-electrolyte interfacial impedance [50]-[52]. However, the CDL for the 3D microtowers with NFS is higher which may be attributed to the increased porosity and surface texturing at the electrode-electrolyte interface. This also causes the overall impedance to be dominated by the double layer capacitance. Interestingly, it is observed that the PVA/PAA NFS did not have an effect on the real part of the impedance at the electrophysiologically relevant frequency of 1 kHz as demonstrated in FIG. 8 (a) but did impact the phase as expected in FIG. 8 (b) due to the aforementioned increase in capacitance. Hence, the technique is capable of introducing a new modality to 3D MEAs device with minimal yet beneficial changes to impedance properties.

Example 4: Antimicrobial Studies for Silver-Functionalized PVA/PAA-NSF

Figure 9:
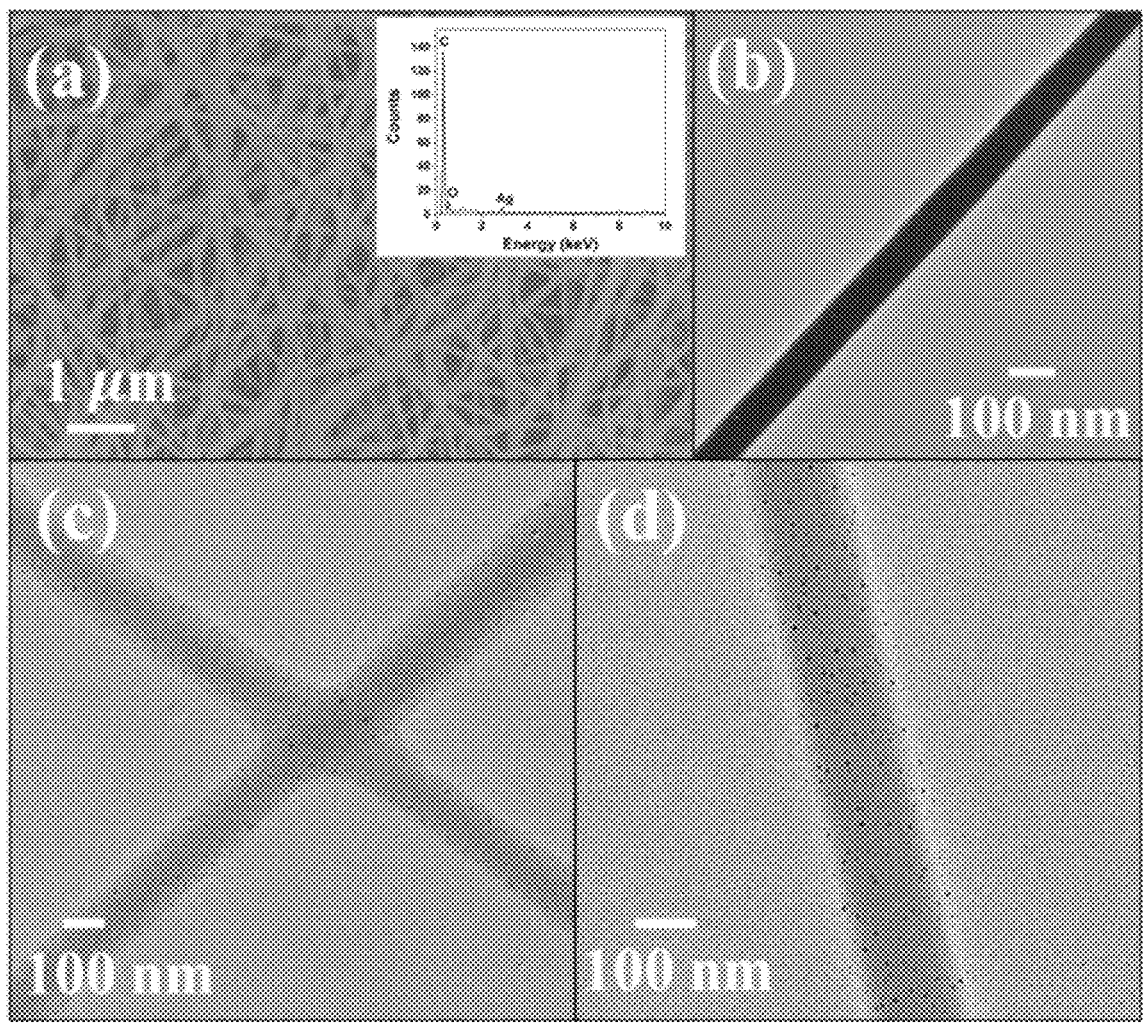
FIG. 9: (a) SEM image with EDS inset of PVA/PAA-NFS with Ag NP clearly depicting an Ag peak even though the silver NPs are not evident in the SEM images. TEM images of PVA/PAA-NFS after heat treatment (b) without Ag NP, (c) with Ag NP formed after electrospinning by reduction (d) Ag NP formed in solution before electrospinning.
Figure 10:
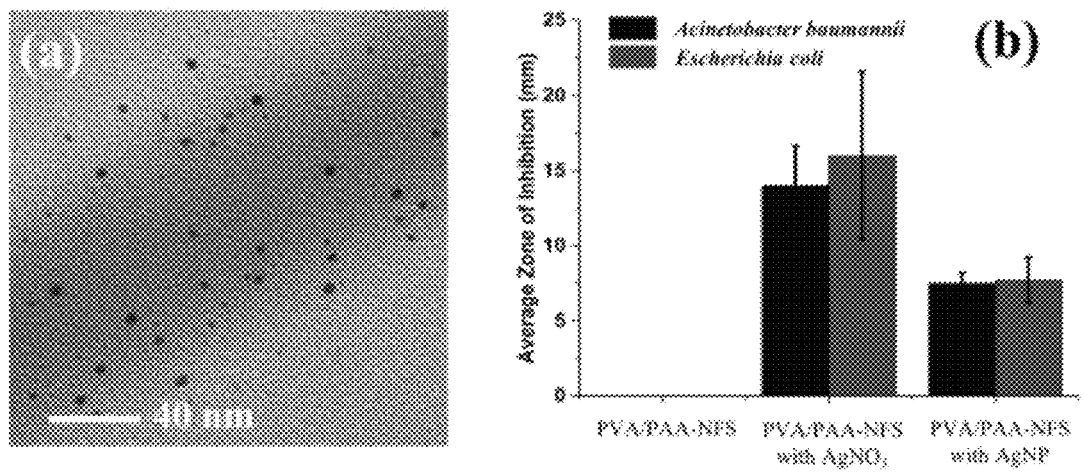
FIG. 10: Characterization of AgNP in PVA/PAA-NFS by (a) TEM showing Ag NP size ranging from ~5-10 nm and (b) bacterial zone of inhibition study demonstrating the successful release of Ag NP from PVA/PAA-NFS acting as a potent antimicrobial for two bacterial strains.

The silver nanoparticle functionalized PVA/PAA nanofibers were studied using SEM imaging [FIG. 9 (a)]. It can be observed that the fibers with Ag NPs incorporated into the electrospinning solution do not visually display any signs of silver nanoparticles. However, the presence of the silver nanoparticles was confirmed using Energy Dispersive X-ray Spectroscopy (EDX), provided in FIG. 9 (a) inset, in conjunction with SEM imaging. This suggested that the Ag NPs are incorporated within the structure of the fibers, rather than on the surface of the nanofibers. Thus, transmission electron microscopy (TEM) was performed to determine size and distribution of Ag NPs within the fibers. TEM images of PVA/PAA nanofibers without Ag NP and with Ag NP are provided in FIGS. 9 (b)-(d). In FIG. 9 (c) PVA/PAA Ag NPs were realized by reduction from the reducing agent NaBH4, however, it was found that Ag NP could also be formed from the reduction from the hydroxyl groups of the PVA within the PVA/PAA nanofibers. A solution of PVA/PAA with AgNO3 was allowed to stir overnight and was electrospun the following day. TEM image of these fibers [FIG. 9 (d)] indicated that this method was additionally successful in achieving Ag nanoparticles similar to the process with the reducing agent. These processes demonstrated the versatility of the electrospinning technique and significance of the chemistry of materials used to create unique fibers that can be tailored to specific applications. For instance, in our study, reducing the nanofibers after electrospinning would not be favorable because the reducing agent would need to be washed away to prevent any detrimental effects on cells. However, these post processing steps can be avoided by the formation of the Ag NP prior to electrospinning with the aid of the electrospinning material as demonstrated. The size of the NPs (~5-15 nm), and distribution of Ag NP within the nanofiber is depicted in FIG. 10 (a). The Ag NP were homogeneously distributed within the nanofiber, which is the darker blurred area in FIG. 10 (a). The interaction of Ag+ with the copolymer resulted in the formation of the nanoparticles inside of the fiber as opposed to the surface of the fiber. The Ag+ ions from AgNO3 had coordinating interactions with the oxygen atoms by electron donation from either PVA hydroxyl group or PAA hydroxyl and carboxyl groups [53]. The release and antimicrobial properties were quantified by comparing the zone of inhibition for three sets of nanofiber mats, PVA/PAA, PVA/PAA with AgNO3, and PVA/PAA with Ag NP shown in FIG. 10 (b). For the first strain of bacteria, *Acinetobacter baumannii*, the zone of inhibition was not present for the PVA/PAA nanofiber control and averaged to be 14 mm for the PVA/PAA nanofibers with AgNO3 incorporated into the solution, and 7.5 mm for the PVA/PAA nanofibers with Ag NP. For the second strain of bacteria, *Escherichia coli*, the zone of inhibition was not present for the PVA/PAA nanofiber control and averaged to be 16 mm for the PVA/PAA nanofibers with AgNO3 incorporated into the solution, and 7.67 mm for the PVA/PAA nanofibers with Ag NP. These bacterial studies confirmed the loading and releasing of Ag nanoparticle as demonstrated by successful antibacterial results. Although the Ag NPs were used as model drugs in this study, it is significant to note the importance of metal nanoparticles and metal ions in the biomedical field. It is known that abnormal homeostatsis of metal ions in cells have been found to be correlated to several types of diseases such as cancer, neurodegenerative disease and diabetes [54]. This study has demonstrated the potential of this multifunctional biosystems platform for the study of disease models by simultaneous release of either metal ions, drugs or even proteins and subsequent monitoring of cellular response [55].

Figure 11:
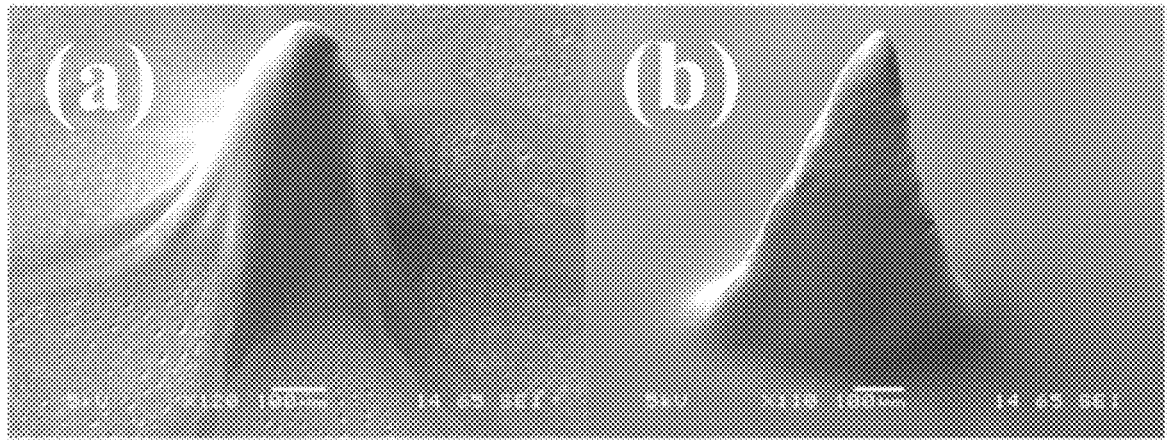
FIG. 11: SEM image of 3D microtower MEA coated with PS: (a) after drop-casting, (b) after drop-casting and spin coating.

Example 5: 3D Insulation Strategy with PS: Optimization and Characterization FIG. 11 (a) shows the SEM image of the PS insulated, metallized 3D microtower with a drop-casted layer of 10% PS solution. Higher concentrations of the PS solution were not used as they would lead to longer drying times causing topographical defects as observed in the glass slides and in this figure. Even with a 10% PS concentration, it is observed that when the PS solution is drop-casted on the 3D printed structure, the PS forms a blanket layer atop the 3D towers upon drying as shown in FIG. 11 (a). A closer look at this image additionally reveals micropores at the base of the towers, formed due to the drop-casted PS solution being thicker around the base of the towers and during the drying of the PS solution, bubbles of the solvent (THF), escape from the PS layer leading to the observed porosity. This problem would only have been aggravated for higher concentrations of PS. This issue however is completely resolved when the samples are spin coated after drop casting. The PS layer is uniform and conformal with the 3D printed tower geometry [FIG. 11 (b)].

Figure 12:
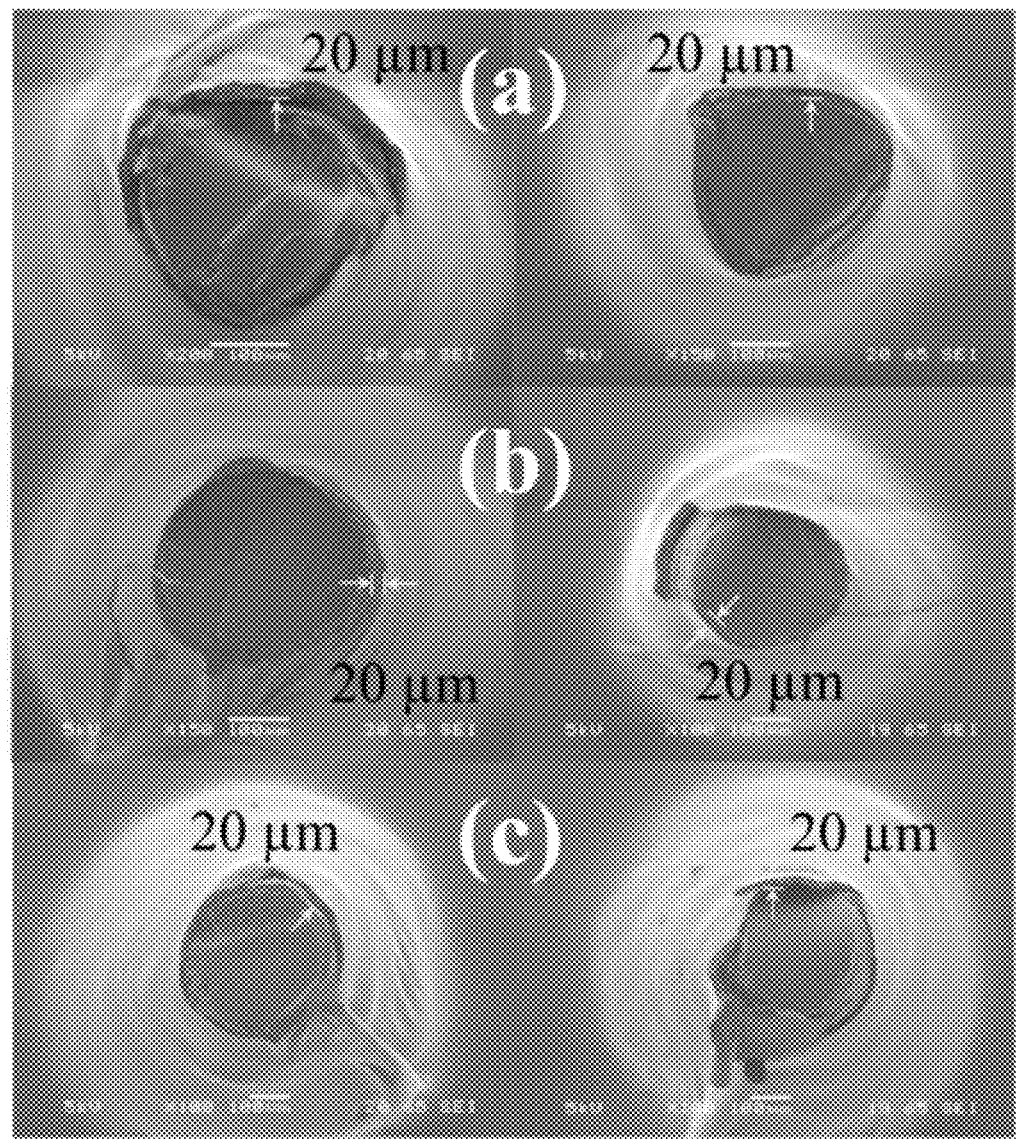
FIG. 12: SEM images of broken tips to determine PS film thickness for (a) 1200 µm, (b) 1600 µm and (c) 2000 µm tall microtowers. An ImageJ scale bar of 20 µm indicates the thickness comparisons in the various heights.

Table 1 summarizes the obtained PS film thicknesses on glass slides for the various concentrations and spin-speeds tested. Film thickness increased as concentration increased and decreased as spin speed increased, both following expected trends. PS concentrations higher that 30% resulted in the formation of "lumps" in the spin-coated device. This data could subsequently be used to define insulation of any desired thickness. However, since the insulation layer technique was intended for 3D structures, conformality had to be demonstrated along the entirety of a 3D topography. To corroborate the translation of the spin-coating parameters from the 2D to 3D regime, 30% PS spincoated at 1000 rpm was employed. A PS concentration of 10% was too low and resulted in a thickness under 5 µm, whereas 40% was too high and resulted in "lumping". Therefore, about 20-30% concentration range was chosen to achieve uniform PS film in 3D (Table 2). FIG. 12 depicts a series of "cleaved tips", exposing the 3D resin and PS film around the diameter of the towers. As depicted in FIG. 12, the thickness of the film was approximately 20 µm for all of the heights tested. This thickness was similar to the thickness obtained in Table 1, given the same parameters, indicating that the coating parameters were valid for 3D topographies up to a height of approximately 2000 µm, representing excellent uniformity.

The observed uniform coverage by PS on 3D structures could be attributed to the low viscosity of the solution enabling it to be mobile and spinning, dispersing the solution along the sides of the towers, and atop the tips, covering any unexposed area. The volatility of the THF permitted the curing and solidification of PS immediately after covering the varied topography, preventing the accumulation of material from a settling process. Although, the PS was relatively uniform, heterogeneity in the film thickness could still be observed along the diameter of the broken tips. For instance, the left tower in FIG. 12 (a) indicates a thinner film towards the bottom as compared to the top of the tower. The top of the tower could have been facing the outer radius of the spin-coater and as the polymer solution flowed, it was collected and subsequently dried in that area. To address this problem, reduced solution volume could be used or the polymer solution can be drop-casted immediately after spinning has started to ensure that the THF does not evaporate instantly.

Figure 13:
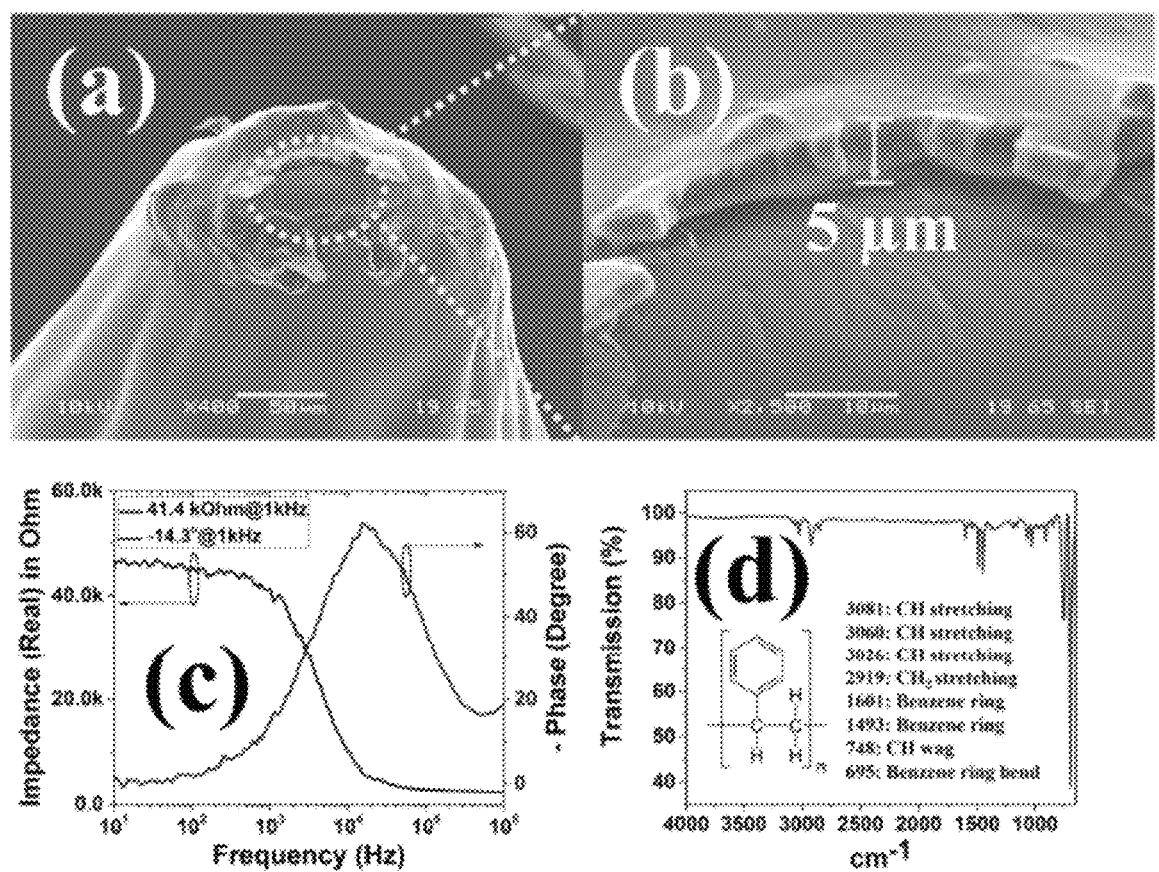
FIG. 13: SEM image of 3D MEAs coated with PS: (a) drop-casted, spin-coated and laser ablated to expose an opening in area of approximately 50×50 µm² (area indicated with box) and (b) close up of ablated area indicates a PS film thickness of ~5 µm. (c) Plot of real and imaginary parts of impedance for 3D MEAs with 50×50 µm2 microelectrodes (d) FTIR analysis of PS film resulting after casting.

From Table 1, it is also apparent that 20% PS, spin-casted either at 1000 rpm or 5000 rpm, would result in the desired film thickness of approximately 5 µm in both 2D and 3D, which is thickness of traditional insulation layers for MEA devices [45]. Once the insulation technique was developed and optimized, it was applied to the fabricated 3D microtower electrodes to realize smaller (50×50 µm2) electrodes. FIG. 13 (a) depicts a close-up SEM image of the 3D tower MEA after drop-casting and spin-coating of 20% PS insulation at 5000 rpm. The recording site in the 3D MEA was defined by laser micromachining and the laser ablated electrode is shown in both FIGS. 13 (a) and (b). The film exposed after laser ablation was measured to be 5 µm, which was as expected from Table 1 given the insulation thickness characterization. Thus, subsequent experiments used these parameters to define the insulation layer on the 3D MEA. This insulation technique was successful due to the low viscosity of the PS solution and high volatility of THF, 2.5:1 vapor density ratio relative to air [56]. The simplicity, thermal budget, biocompatibility and rapid definition of 3D insulation using PS provides a significant advantage over traditional insulation materials such as SU-8 and PDMS.

FIG. 13 (c) depicts the full spectrum impedance and phase response (N=2) of the 50×50 µm2 3D MEAs after PS insulation and laser micromachining. The reduction of the microelectrode size results in a significant increase in the impedance to 41.4 kΩ at 1 kHz. The phase signature of the smaller electrodes is also shown in the same figure and it is observed that the smaller size of the electrodes causes them to have a lower value of CDL, which manifests in the resistive behavior of the MEAs at frequencies up to 100 Hz. As the frequency increases the effect of CDL becomes more pronounced and the electrode-electrolyte interfacial impedance becomes dominated by capacitance. However, at higher frequencies the solution resistance starts to dominate the response which is also observed for the 3D microtower MEAs making the phase response resistive, all observations matching microelectrode theory [50]-[52].

FIG. 13 (d) provides the FTIR of the PS coated on the 3D MEA. Some noteworthy peaks from the PS FTIR are: the 695 cm-1 peak from a ring bend indicating that the molecule is monosubstituted and the 748 cm-1 peak from C—H wag signifying a C—H bond to a benzene ring, both of which are characteristic peaks of polystyrene.

SUMMARY OF RESULTS AND RELATED CONSIDERATIONS

As noted by the above disclosure, a microfabrication technique has been developed that is capable of rapidly realizing 3D MEAs, which are highly versatile and fully functional for 3D cell culture applications. With a union between makerspace microfabrication coupled with standard microfabrication technologies as needed, we have demonstrated the realization of 3D microtowers of base diameter, 250 µm and height of 400 µm. A "coarse insulation layer" was defined with a biocompatible laminate exposing these microtowers. This platform provides for a device ready for applications of cell/tissue growth, proliferation and long-term cultures in-vitro.

Development of biocompatible 3D scaffolds atop the 3D microtower was performed with two types of materials: PET and PVA/PAA. PET-NFS resulted in slight beading and larger range in fiber width, whereas PVA/PAA-NFS were found to be homogenous fiber widths with no beading. Thus, PVA/PAA-NFS was more favorable than PET-NFS in the intended application as a scaffold atop of the 3D printed MEA platform. Impedance measurements of devices with integrated PVA/PAA-NFS demonstrated no significant change with and without nanofibers, indicating that the introduction of the new modality to the device did not interfere with the electrical characteristics of the MEA. In order to demonstrate enhanced functionality as a potential drug delivery system in addition to biosensing, the PVA/PAA NFS were loaded with ~5-15 nm Ag NP.

The Ag NP served as a model drug and was characterized by TEM and release was confirmed by the bacterial-inhibition zone studies with two different types of bacteria, *Acinetobacter baumannii* and *Escherichia coli*. This study displayed the versatility of nanofibers integrated with the 3D MEAs in applications, especially as multi-functional sensors.

Due to the requirement of small electrode areas for MEAs, a "fine insulation technique" was developed for the 3D structures. PS in THF was spin-coated on 3D towers and was found to result in uniform coating that can be tailored in thickness from 1-20 μm. This technique was subsequently employed on a functional 3D microtower device to reduce electrode sizes (50×50 μm2 electrodes) utilizing a laser micromachining step. SEM imaging and impedance measurements confirmed the definition of the microelectrodes and impedance properties to match other reported 3D MEAs. These multi-functional 3D MEA platforms are not limited to applications in 3D cell-culture, biosensing and pharmaceutical screening but can be utilized as potential gas-sensors, environmental sensors, in vitro agricultural sensors and drug delivery platforms.

TABLE 1

Summary of film thicknesses resulting from various Polystyrene (PS) concentrations and spin-speeds in planer dimension.

| Concentration of | Film Thickness | | |
|---|---|---|---|
| PS in THF (w/v) | 500 rpm | 1000 rpm | 5000 rpm |
| 10% | 0.9189 μm | 0.9602 μm | 0.8063 μm |
| error | 0.198 μm | 0.327 μm | 0.044 μm |
| 20% | 5.427 μm | 5.109 μm | 4.178 μm |
| error | 0.944 μm | 0.345 μm | 0.772 μm |
| 30% | 47.925 μm | 23.694 μm | 8.801 μm |
| error | 17.560 μm | 5.994 μm | 0.580 μm |
| 40% | Lumped | 75.993 μm | 31.457 μm |
| error | NA | 20.522 μm | 3.187 μm |

TABLE 2

Summary of film thicknesses resulting from various Polystyrene (PS) concentrations and spin-speeds in three-dimension.

| Concentration of PS in THF (w/v) | Film Thickness (μm) |
|---|---|
| 20% | 4.578 @ 5000 rpm |
| error | 0.652 |
| 30% | 18.617 @ 1000 rpm |
| error | 4.442 |

Notwithstanding that the numerical ranges and parameters setting forth the broad scope are approximations, the numerical values set forth in specific non-limiting examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. As a non-limiting example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 7.

It should be borne in mind that all patents, patent applications, patent publications, technical publications, scientific publications, and other references referenced herein are hereby incorporated by reference in this application in order to more fully describe the state of the art to which the present invention pertains.

Reference to particular buffers, media, reagents, cells, culture conditions and the like, or to some subclass of same, is not intended to be limiting, but should be read to include all such related materials that one of ordinary skill in the art would recognize as being of interest or value in the particular context in which that discussion is presented. For example, it is often possible to substitute one buffer system or culture medium for another, such that a different but known way is used to achieve the same goals as those to which the use of a suggested method, material or composition is directed. It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While one or more embodiments of the present invention have been shown and described herein, such embodiments are provided by way of example only. Variations, changes and substitutions may be made without departing from the invention herein. Accordingly, it is intended that the invention be limited only by the spirit and scope of the appended claims. The teachings of all references cited herein are incorporated in their entirety to the extent not inconsistent with the teachings herein.

REFERENCES

[1] N. Azim, T. Ausaf, A. Kundu, L. Zhai, and S. Rajaraman, "Fabrication and Characterization of 3D Printed, 3D Microelectrode Arrays With Spin Coated Insulation and Functional Electrospun 3D Scaffolds for 'Disease in a Dish' and 'Organ on a Chip' Models," in *Solid-State Sensors, Actuators and Microsystems Workshop*, 2018, pp. 124-127.

[2] F. M. Watt and W. T. S. Huck, "Role of the extracellular matrix in regulating stem cell fate," *Nat. Rev. Mol. Cell Biol.*, vol. 14, no. 8, pp. 467-473, August 2013.

[3] E. Knight and S. Przyborski, "Advances in 3D cell culture technologies enabling tissue-like structures to be created in vitro," *J. Anat.*, vol. 227, no. 6, pp. 746-756, December 2015.

[4] M. W. Tibbitt and K. S. Anseth, "Hydrogels as extracellular matrix mimics for 3D cell culture," *Biotechnol. Bioeng.*, vol. 103, no. 4, pp. 655-663, July 2009.

[5] B. A. Justice, N. A. Badr, and R. A. Felder, "3D cell culture opens new dimensions in cell-based assays," *Drug Discov. Today*, vol. 14, no. 1-2, pp. 102-107, January 2009.

[6] K. Duval et al., "Modeling Physiological Events in 2D vs. 3D Cell Culture," *Physiology*, vol. 32, no. 4, pp. 266-277, July 2017.

[7] A. Blau, "Cell adhesion promotion strategies for signal transduction enhancement in microelectrode array in vitro electrophysiology: An introductory overview and critical discussion," *Curr. Opin. Colloid Interface Sci.*, vol. 18, no. 5, pp. 481-492, October 2013.

[8] A. Diaz Lantada, D. Curras, J. Mousa, and S. Hengsbach, "Tissue Engineering Scaffolds for 3D Cell Culture," Humana Press, 2016, pp. 249-268.

[9] P. Zorlutuna et al., "Microfabricated Biomaterials for Engineering 3D Tissues," *Adv. Mater.*, vol. 24, no. 14, pp. 1782-1804, April 2012.

[10] R. Kim, S. Joo, H. Jung, N. Hong, and Y. Nam, "Recent trends in microelectrode array technology for in vitro neural interface platform," *Biomed. Eng. Lett.*, vol. 4, no. 2, pp. 129-141, June 2014.

[11] E. Masi et al., "Electrical spiking in bacterial biofilms," *J. R. Soc. Interface*, vol. 12, no. 102, p. 20141036, January 2015.

[12] P. Ruther et al., "The NeuroProbes Project-Multifunctional Probe Arrays for Neural Recording and Stimulation," *Proc. 13th Annu. Conf. IFESS, September 21-25, Freiburg, Ger.*, vol. 53, pp. 238-240, 2008.

[13] S. Rajaraman, S.-O. Choi, M. A. McClain, J. D. Ross, M. C. LaPlaca, and M. G. Allen, "Metal-Transfer-Micromolded Three-Dimensional Microelectrode Arrays for in-vitro Brain-Slice Recordings," *J. Microelectromechanical Syst.*, vol. 20, no. 2, pp. 396-409, April 2011.

[14] S. Rajaraman et al., "Microfabrication technologies for a coupled three-dimensional microelectrode, microfluidic array," *J. Micromechanics Microengineering*, vol. 17, no. 1, pp. 163-171, January 2007.

[15] L. Sileo et al., "Electrical coupling of mammalian neurons to microelectrodes with 3D nanoprotrusions," *Microelectron. Eng.*, vol. 111, pp. 384-390, November 2013.

[16] N. Shmoel, N. Rabieh, S. M. Ojovan, H. Erez, E. Maydan, and M. E. Spira, "Multisite electrophysiological recordings by self-assembled loose-patch-like junctions between cultured hippocampal neurons and mushroom-shaped microelectrodes," *Sci. Rep.*, vol. 6, no. 1, p. 27110, July 2016.

[17] A. Kundu, T. Ausaf, and S. Rajaraman, "3D Printing, Ink Casting and Micromachined Lamination (3D PICLμM): A Makerspace Approach to the Fabrication of Biological Microdevices," *Micromachines*, vol. 9, no. 2, p. 85, February 2018.

[18] N. Bhardwaj and S. C. Kundu, "Electrospinning: A fascinating fiber fabrication technique," *Biotechnol. Adv.*, vol. 28, no. 3, pp. 325-347, May 2010.

[19] A. Baji, Y. W. Mai, S. C. Wong, M. Abtahi, and P. Chen, "Electrospinning of polymer nanofibers: Effects on oriented morphology, structures and tensile properties," *Compos. Technol.*, vol. 70, no. 5, pp. 703-718, 2010.

[20] J. Lannutti, D. Reneker, T. Ma, D. Tomasko, and D. Farson, "Electrospinning for tissue engineering scaffolds," *Mater. Sci. Eng. C*, vol. 27, no. 3, pp. 504-509, April 2007.

[21] Y. Liu et al., "Electrospun Three-Dimensional Nanofibrous Structure via Probe Arrays Inducing," *Micromachines*, vol. 9, no. 9, p. 427, August 2018.

[22] S. Xiao, M. Shen, R. Guo, S. Wang, and X. Shi, "Immobilization of Zerovalent Iron Nanoparticles into Electrospun Polymer Nanofibers: Synthesis, Characterization, and Potential Environmental Applications," *J. Phys. Chem. C*, vol. 113, no. 42, pp. 18062-18068, October 2009.

[23] H. Y. Son, J. H. Ryu, H. Lee, and Y. S. Nam, "Silver-polydopamine hybrid coatings of electrospun poly(vinyl alcohol) nanofibers," *Macromol. Mater. Eng.*, vol. 298, no. 5, pp. 547-554, May 2013.

[24] K. H. Hong, J. L. Park, I. N. Hwan Sul, J. H. Youk, and T. J. Kang, "Preparation of antimicrobial poly(vinyl alcohol) nanofibers containing silver nanoparticles," *J. Polym. Sci. Part B Polym. Phys.*, vol. 44, no. 17, pp. 2468-2474, September 2006.

[25] A. Malhotra, T. Bera, and L. Zhai, "Bioinspired Metal Ion Coordinated Polyelectrolyte Fibrous Nanoreactors," *Adv. Mater. Interfaces*, vol. 3, no. 22, p. 1600692, November 2016.

[26] A. Chunder, S. Sarkar, Y. Yu, and L. Zhai, "Fabrication of ultrathin polyelectrolyte fibers and their controlled release properties," *Colloids Surfaces B Biointerfaces*, vol. 58, no. 2, pp. 172-179, August 2007.

[27] D. An et al., "Developing robust, hydrogel-based, nanofiber-enabled encapsulation devices (NEEDs) for cell therapies," *Biomaterials*, vol. 37, pp. 40-48, January 2015.

[28] K. M. M. Abou El-Nour, A. Eftaiha, A. Al-Warthan, and R. A. A. Ammar, "Synthesis and applications of silver nanoparticles," *Arab. J. Chem.*, vol. 3, no. 3, pp. 135-140, July 2010.

[29] N. Durán, M. Durán, M. B. de Jesus, A. B. Seabra, W. J. Fávaro, and G. Nakazato, "Silver nanoparticles: A new view on mechanistic aspects on antimicrobial activity," *Nanomedicine Nanotechnology, Biol. Med.*, vol. 12, no. 3, pp. 789-799, April 2016.

[30] M. Rai, A. Yadav, and A. Gade, "Silver nanoparticles as a new generation of antimicrobials," *Biotechnol. Adv.*, vol. 27, no. 1, pp. 76-83, January 2009.

[31] Y. Cao, D. Li, C. Shang, S.-T. Yang, J. Wang, and X. Wang, "Threedimensional culture of human mesenchymal stem cells in a polyethylene terephthalate matrix," *Biomed. Mater.*, vol. 5, no. 6, p. 065013, December 2010.

[32] Y. Li, T. Ma, S. T. Yang, and D. A. Kniss, "Thermal compression and characterization of three-dimensional nonwoven PET matrices as tissue engineering scaffolds," *Biomaterials*, vol. 22, no. 6, pp. 609-618, March 2001.

[33] J. Santiago-Morales, G. Amariei, P. Leton, and R. Rosal, "Antimicrobial activity of poly(vinyl alcohol)-poly (acrylic acid) electrospun nanofibers," *Colloids Surfaces B Biointerfaces*, vol. 146, pp. 144-151, October 2016.

[34] J.-C. Park et al., "Electrospun poly(vinyl alcohol) nanofibers: effects of degree of hydrolysis and enhanced water stability," *Polym. J.*, vol. 42, no. 3, pp. 273-276, March 2010.

[35] S. Kumagai, T. Yamamoto, H. Kubo, and M. Sasaki, "Photoresist spray coating for 3D MEMS/NEMS," in *2012 IEEE Nanotechnology Materials and Devices Conference, IEEE NMDC 2012*, 2012, pp. 124-127.

[36] N. P. Pham, J. N. Burghartz, and P. M. Sarro, "Spray coating of photoresist for pattern transfer on high topography surfaces," *J. Micromechanics Microengineering*, vol. 15, no. 4, pp. 691-697, April 2005.

[37] D. S. Ginger, H. Zhang, and C. A. Mirkin, "The Evolution of Dip-Pen Nanolithography," *Angew. Chemie—Int. Ed.*, vol. 43, no. 1, pp. 30-45, January 2004.

[38] M. E. Alf et al., "Chemical vapor deposition of conformal, functional, and responsive polymer films," *Adv. Mater.*, vol. 22, no. 18, pp. 1993-2027, December 2010.

[39] A. B. Frazier and M. G. Allen, "High aspect ratio electroplated microstructures using a photosensitive polyimide process," in [1992] *Proceedings IEEE Micro Electro Mechanical Systems*, 1992, pp. 87-92.

[40] B. Ghane-Motlagh and M. Sawan, "Design and Implementation Challenges of Microelectrode Arrays: A Review," *Mater. Sci. Appl.*, vol. 04, no. 08, pp. 483-495, July 2013.

[41] N. Atthi et al., "Improvement of Photoresist Film Coverage on High Topology Surface with Spray Coating Technique," 2010.

[42] T. M. Nargang et al., "Liquid polystyrene: a room-temperature photocurable soft lithography compatible pour-and-cure-type polystyrene," *Lab Chip*, vol. 14, no. 15, pp. 2698-2708, July 2014.

[43] Formlabs, "Materials Data Sheet Photopolymer Resin for Form 1+ and Form 2 FORMLABS MATERIAL PROPERTIES," 2017.

[44] A. W. Bauer, W. M. Kirby, J. C. Sherris, and M. Turck, "Antibiotic susceptibility testing by a standardized single disk method.," *Am. J. Clin. Pathol.*, vol. 45, no. 4, pp. 493-6, April 1966.

[45] "Cell-based biosensor array and associated methods for manufacturing the same," August 2015.

[46] S. Rajaraman et al., "Three-Dimensional Metal Transfer Micromolded Microelectrode Arrays (MEAS) for In-Vitro Brain Slice Recordings," in *TRANSDUCERS 2007-2007 International Solid-State Sensors, Actuators and Microsystems Conference*, 2007, pp. 1251-1254.

[47] W. Wang et al., "Enhancing the hydrophilicity and cell attachment of 3D printed PCL/graphene scaffolds for bone tissue engineering," *Materials (Basel).*, vol. 9, no. 12, p. 992, December 2016.

[48] Z. Ma, M. Kotaki, T. Yong, W. He, and S. Ramakrishna, "Surface engineering of electrospun polyethylene terephthalate (PET) nanofibers towards development of a new material for blood vessel engineering," *Biomaterials*, vol. 26, no. 15, pp. 2527-2536, May 2005.

[49] J. Xie, M. R. MacEwan, W. Z. Ray, W. Liu, D. Y. Siewe, and Y. Xia, "Radially Aligned, Electrospun Nanofibers as Dural Substitutes for Wound Closure and Tissue Regeneration Applications," *ACS Nano*, vol. 4, no. 9, pp. 5027-5036, September 2010.

[50] D. a Borkholder, "Cell Based Biosensors using Microelectrodes," *PhD thesis*, pp. 1-253, 1998.

[51] W. Franks, I. Schenker, P. Schmutz, and A. Hierlemann, "Impedance characterization and modeling of electrodes for biomedical applications," *IEEE Trans. Biomed. Eng.*, vol. 52, no. 7, pp. 1295-1302, July 2005.

[52] D. A. Borkholder, J. Bao, N. I. Maluf, E. R. Perl, and G. T. A. Kovacs, "Microelectrode arrays for stimulation of neural slice preparations," *J. Neurosci. Methods*, vol. 77, no. 1, pp. 61-66, November 1997.

[53] K. Hwa Hong, J. Lyoul Park, I. Hwan Sul, J. H. Youk, and T. Jin Kang, "Preparation of Antimicrobial Poly(vinyl alcohol) Nanofibers Containing Silver Nanoparticles," *J Polym Sci Part B Polym Phys,* vol. 44, pp. 2468-2474, 2006.

[54] X. Qian and Z. Xu, "Fluorescence imaging of metal ions implicated in diseases," *Chem. Soc. Rev.*, vol. 44, no. 14, pp. 4487-4493, July 2015.

[55] S. Babitha et al., "Electrospun protein nanofibers in healthcare: A review," *Int. J. Pharm.*, vol. 523, no. 1, pp. 52-90, May 2017.

[56] R. J. Lewis and N. I. (Newton I. Sax, *Sax's Dangerous Properties of Industrial Materials*. J. Wiley & Sons, 2004.

What is claimed is:

1. A microelectrode platform comprising:
a platform comprising a plurality of microtower electrodes, wherein each of the plurality of microtower electrodes comprises a tip,
a metallic layer disposed on each of the plurality of microtower electrodes;
a biocompatible layer disposed on the platform, wherein the biocompatible layer comprises a plurality of apertures arranged to correspond with the tip of each of the plurality of microtower electrodes; and
a plurality of interconnected nano-scaffolds disposed in a three-dimensional pattern above the tip of each of the plurality of microtower electrodes, wherein the interconnected nano-scaffolds comprise radially aligned fibers extending out from the tip of at least one microtower electrode, and
wherein a first impedance of the microtower electrodes with nano-scaffolds is within a ten percent variance relative to a second impedance of the microtower electrodes without nanoscaffolds, when the first impedance and the second impedance are measured at the same frequency selected from a range of 800 Hz to 1000 KHz.

2. The microelectrode platform according to claim 1, wherein the metallic layer comprises one selected from titanium, gold, and combinations thereof.

3. The microelectrode platform according to claim 1, wherein the metallic layer has a thickness of from about 10 nm to about 100 nm.

4. The microelectrode platform according to claim 1, wherein each of the plurality of interconnected nano-scaffolds comprises one selected from the group consisting of polyvinyl alcohol (PVA), polyacrylic acid (PAA), polyethylene terephthalate (PET), combinations thereof, and copolymers thereof.

5. The microelectrode platform according to claim 1, further comprising a plurality of nanoparticles embedded into the each of the plurality of interconnected nano-scaffolds.

6. The microelectrode platform according to claim 5, wherein the plurality of nanoparticles have a bioactive agent.

7. The microelectrode platform according to claim 6, wherein the bioactive agent is one selected from the group consisting of a drug, an antimicrobial agent, an antiviral agent, an antibiotic agent, and combinations thereof.

8. The microelectrode platform according to claim 5, wherein the plurality of nanoparticles exhibit an inhibitory effect toward one selected from the group consisting of *Acinetobacter baumannii*, *Escherichia coli*, and combinations thereof.

9. The microelectrode platform according to claim 5, wherein the plurality of nanoparticles comprise silver.

10. The microelectrode platform according to claim 1, wherein the biocompatible laminate layer comprises an insulating polymeric material.

11. The microelectrode platform according to claim 1, further comprising one or more bioactive agents embedded into the each of the plurality of interconnected nano-scaffolds.

12. The microelectrode platform according to claim 10, wherein the insulating layer is about 0.5-30 μm thick.

13. The microelectrode platform according to claim 10, wherein the insulating polymeric is ablated to produce the plurality of apertures, wherein optionally, one or more of the plurality of apertures comprises a dimension of about 30-70×30-70 μm².

* * * * *